US011018068B2

(12) United States Patent
Liu et al.

(10) Patent No.: US 11,018,068 B2
(45) Date of Patent: May 25, 2021

(54) METHODS AND APPARATUSES FOR PACKAGING AN ULTRASOUND-ON-A-CHIP

(71) Applicant: Butterfly Network, Inc., Guilford, CT (US)

(72) Inventors: Jianwei Liu, Fremont, CA (US); Keith G. Fife, Palo Alto, CA (US)

(73) Assignee: Butterfly Network, Inc., Guilford, CT (US)

( * ) Notice: Subject to any disclaimer, the term of this patent is extended or adjusted under 35 U.S.C. 154(b) by 0 days.

(21) Appl. No.: 16/502,553

(22) Filed: Jul. 3, 2019

(65) Prior Publication Data

US 2020/0013691 A1 Jan. 9, 2020

Related U.S. Application Data

(60) Provisional application No. 62/694,810, filed on Jul. 6, 2018.

(51) Int. Cl.
| | |
|---|---|
| *H01L 23/31* | (2006.01) |
| *H01L 23/498* | (2006.01) |
| *H01L 21/56* | (2006.01) |
| *H01L 23/00* | (2006.01) |
| *A61B 8/00* | (2006.01) |

(52) U.S. Cl.
CPC ............ *H01L 23/3128* (2013.01); *A61B 8/44* (2013.01); *H01L 21/568* (2013.01); *H01L 23/49816* (2013.01); *H01L 23/49822* (2013.01); *H01L 23/49827* (2013.01); *H01L 23/49894* (2013.01); *H01L 24/32* (2013.01); *H01L 24/83* (2013.01); *H01L 24/16* (2013.01); *H01L 24/73* (2013.01); *H01L 2224/16235* (2013.01);

(Continued)

(58) Field of Classification Search
CPC . B06B 1/0292; B81B 3/0021; H01L 2924/14; H01L 2224/4813; H01L 2225/06541
USPC .......... 257/723, 693, E23.116; 438/107, 127
See application file for complete search history.

(56) References Cited

U.S. PATENT DOCUMENTS

| | | |
|---|---|---|
| 7,741,686 B2 | 6/2010 | Khuri-Yakub et al. |
| 7,825,509 B1 | 11/2010 | Baumhauer, Jr. et al. |

(Continued)

FOREIGN PATENT DOCUMENTS

WO   WO 2018/165235 A1   9/2018

OTHER PUBLICATIONS

PCT/US2019/040516, Oct. 29, 2019, International Search Report and Written Opinion.

(Continued)

*Primary Examiner* — Jonathan Han
(74) *Attorney, Agent, or Firm* — Wolf, Greenfield & Sacks, P.C.

(57) ABSTRACT

Described herein are methods and apparatuses for packaging an ultrasound-on-a-chip. An ultrasound-on-a-chip may be coupled to a redistribution layer and to an interposer layer. Encapsulation may encapsulate the ultrasound-on-a-chip device and first metal pillars may extend through the encapsulation and electrically couple to the redistribution layer. Second metal pillars may extend through the interposer layer. The interposer layer may include aluminum nitride. The first metal pillars may be electrically coupled to the second metal pillars. A printed circuit board may be coupled to the interposer layer.

16 Claims, 44 Drawing Sheets

(52) U.S. Cl.
CPC ............ *H01L 2224/32225* (2013.01); *H01L 2224/73253* (2013.01); *H01L 2224/8384* (2013.01)

(56) References Cited

U.S. PATENT DOCUMENTS

| | | |
|---|---|---|
| 7,846,102 B2 | 12/2010 | Kupnik |
| 8,076,739 B2 | 12/2011 | Schmollngruber et al. |
| 8,193,685 B2 | 6/2012 | Klee et al. |
| 8,207,652 B2 | 6/2012 | Baumgartner et al. |
| 9,067,779 B1 | 6/2015 | Rothberg et al. |
| 9,242,275 B2 | 1/2016 | Rothberg et al. |
| 9,499,392 B2 | 11/2016 | Rothberg et al. |
| 9,505,030 B2 | 11/2016 | Rothberg et al. |
| 9,922,896 B1 | 3/2018 | Cheng et al. |
| 10,856,844 B2 | 12/2020 | Fife et al. |
| 2004/0184219 A1* | 9/2004 | Otsuka .............. H01L 23/49816 361/306.3 |
| 2006/0055024 A1* | 3/2006 | Wehrly, Jr. ............ H01L 25/105 257/693 |
| 2009/0148967 A1 | 6/2009 | Wodnicki et al. |
| 2010/0133704 A1* | 6/2010 | Marimuthu ............. H01L 24/16 257/778 |
| 2011/0055447 A1 | 3/2011 | Costa |
| 2014/0113156 A1 | 4/2014 | Jonczyk et al. |
| 2016/0009544 A1* | 1/2016 | Rothberg .............. B81B 3/0021 257/737 |
| 2016/0038974 A1 | 2/2016 | Gubbini et al. |
| 2016/0133600 A1 | 5/2016 | Shen et al. |
| 2016/0280538 A1* | 9/2016 | Rothberg ............. A61B 8/4483 |
| 2017/0365774 A1 | 12/2017 | Rothberg et al. |
| 2018/0364201 A1 | 12/2018 | Rothberg et al. |
| 2018/0369862 A1 | 12/2018 | Alie et al. |
| 2019/0231312 A1 | 8/2019 | Fife et al. |
| 2019/0275561 A1 | 9/2019 | Fife et al. |
| 2019/0336103 A1 | 11/2019 | Fife et al. |

OTHER PUBLICATIONS

Invitation to Pay Additional Fees mailed Aug. 22, 2019 in connection with International Application No. PCT/US2019/040516.
International Search Report and Written Opinion dated Oct. 29, 2019 in connection with International Application No. PCT/US2019/040516.
PCT/US2019/040516, Aug. 22, 2019, Invitation to Pay Additional Fees.
International Preliminary Report on Patentability dated Jan. 21, 2021 in connection with International Application No. PCT/US2019/040516.

* cited by examiner

FIG. 21

METHODS AND APPARATUSES FOR PACKAGING AN ULTRASOUND-ON-A-CHIP

CROSS-REFERENCE TO RELATED APPLICATION

The present application claims the benefit under 35 U.S.C. § 119(e) of U.S. Provisional Application Ser. No. 62/694,810, filed Jul. 6, 2018, and entitled "METHODS AND APPARATUSES FOR PACKAGING AN ULTRASOUND-ON-A-CHIP," which is hereby incorporated herein by reference in its entirety.

FIELD

Generally, the aspects of the technology described herein relate to ultrasound devices. Some aspects relate to packaging an ultrasound-on-a-chip.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using an ultrasound imaging device), sound waves are reflected off the tissue, with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound devices, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to at least one aspect, an apparatus is provided. The apparatus comprises: an ultrasound-on-a-chip comprising a top surface and a bottom surface; an interposer layer comprising a top surface and a bottom surface; and a redistribution layer; wherein: the top surface of the ultrasound-on-a-chip device is coupled to the redistribution layer; and the bottom surface of the ultrasound-on-a chip device is coupled to the top surface of the interposer layer.

According to at least one aspect, a method is provided. The method comprises: coupling an interposer layer comprising first metal pillars to a printed circuit board; and coupling the interposer layer to a packaged ultrasound-on-a-chip containing second metal pillars.

According to at least one aspect, a method is provided. The method comprises: forming metal pillars in an interposer layer; coupling the interposer layer to an ultrasound-on-a-chip; and forming a redistribution layer on the ultrasound-on-a-chip.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIGS. 1-37 illustrate cross-sections of various structures during packaging of an ultrasound-on-a-chip device using one process, in accordance with certain embodiments described herein;

DETAILED DESCRIPTION

Conventional ultrasound systems are large, complex, and expensive systems that are typically only purchased by large medical facilities with significant financial resources. Recently, cheaper, portable, and less complex ultrasound imaging devices have been introduced. Such imaging devices may include ultrasonic transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application), which is incorporated by reference herein in its entirety.

The inventors have recognized features that may be helpful for packaging such ultrasound-on-a-chip devices compared with other packaging methods such as wirebonding. In particular, the inventors have recognized that integrated fan-out (InFO) packaging and interposer layers augmented with metal pillars may provide benefits for packaging ultrasound-on-a-chip devices. Example benefits include lower parasitic inductance and resistance, higher efficiency, less heating, higher packaging throughput, and improved packaging reliability. Additionally, such packaging may enable devices to have smaller sensor heads, which may be helpful for ultrasound imaging applications such as cardiac applications where it may be desirable for the sensor head to fit between ribs. Also, such packaging may enable devices to have thinner lenses, which may increase signal intensity.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

Figure 1:
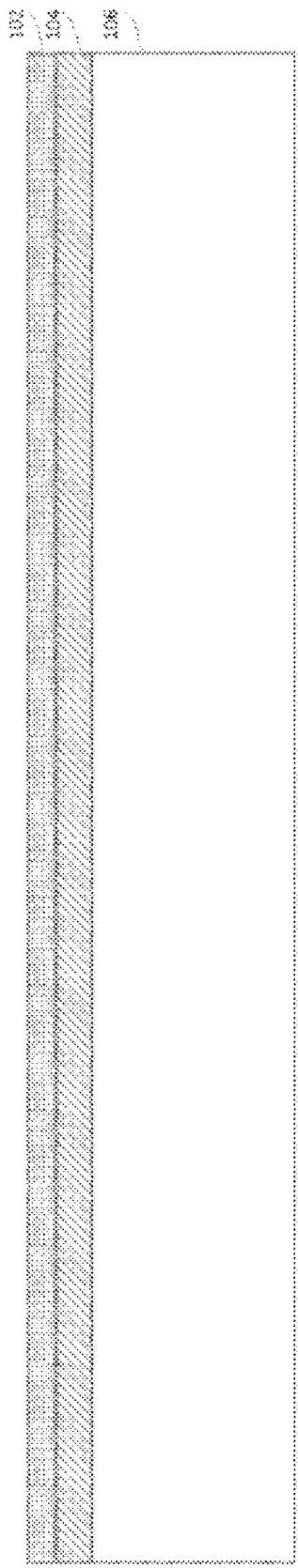

FIGS. 1-37 illustrate cross-sections of various structures during packaging of an ultrasound-on-a-chip device using one process, in accordance with certain embodiments described herein. FIG. 1 illustrates a release layer 104 coupled to a carrier substrate 106, and an insulating layer 102 coupled to the release layer 104. The carrier substrate 106 may include, for example, glass. The release layer 104 may include, for example, light-to-heat-conversion (LTHC)

coating material. The insulating material 102 may include, for example, a polymer that can be patterned with light exposure and developed, such as polyimide, polybenzoxazole (PBO), or benzocyclobutene (BCB).

Figure 2:
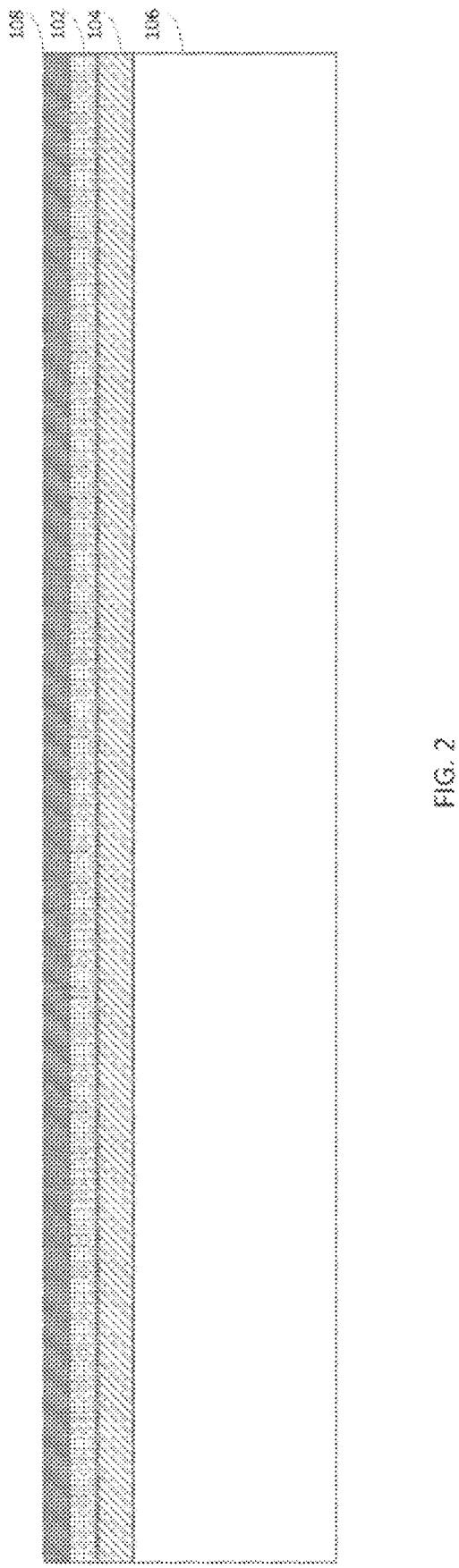

In FIG. 2, a metal layer 108 is formed on the insulating layer 102. The metal layer 108 may be formed, for example, using physical vapor deposition (PVD) or sputtering. The metal layer 108 may include, for example, copper, or in some embodiments, the metal layer 108 may include two layers, such as a titanium layer coupled to the insulating layer 102 and a copper layer coupled to the titanium layer.

Figure 3:
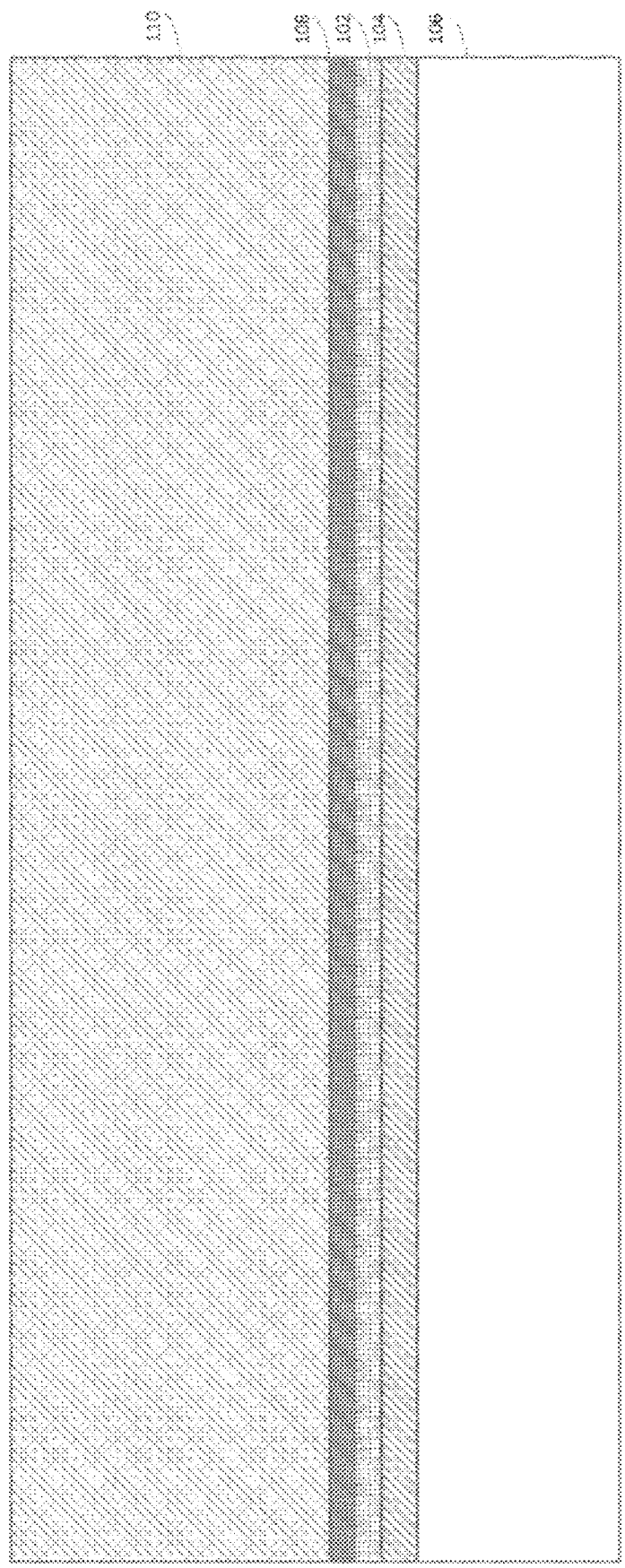

In FIG. 3, a resist layer 110 is formed on the metal layer 108. For example, the resist layer 110 may include photoresist.

Figure 4:
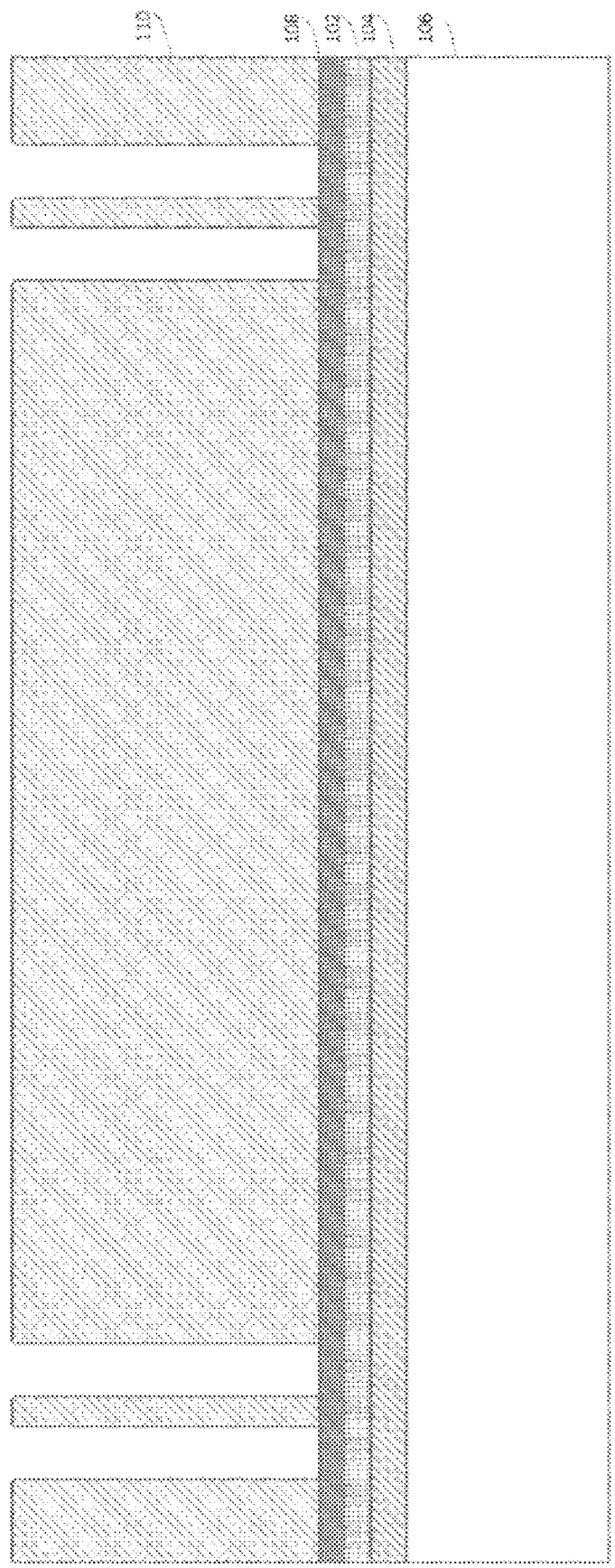

In FIG. 4, openings are formed in the resist layer 110. For example, light exposure through a lithography mask followed by development may create openings in portions of the resist layer 110 that were exposed to light through the mask.

Figure 5:
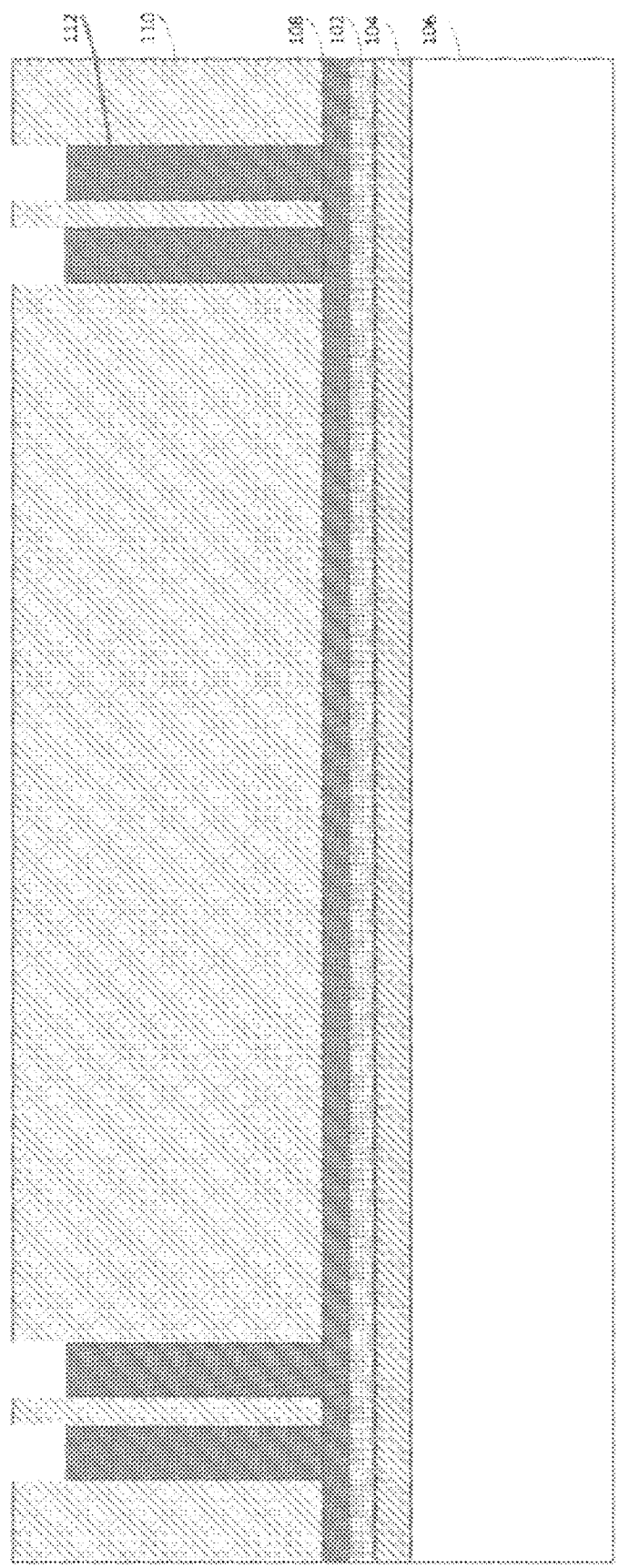

In FIG. 5, metal pillars 112 are formed in the openings in the resist layer 110 using electroplating. The metal layer 108 may serve as a seed layer for the electroplating. The metal pillars 112 may include the same material as the metal layer 108, such as copper. It should be appreciated that while four metal pillars 112 are shown, there may be more metal pillars 112 (e.g., tens or hundreds) arranged two-dimensionally.

Figure 6:
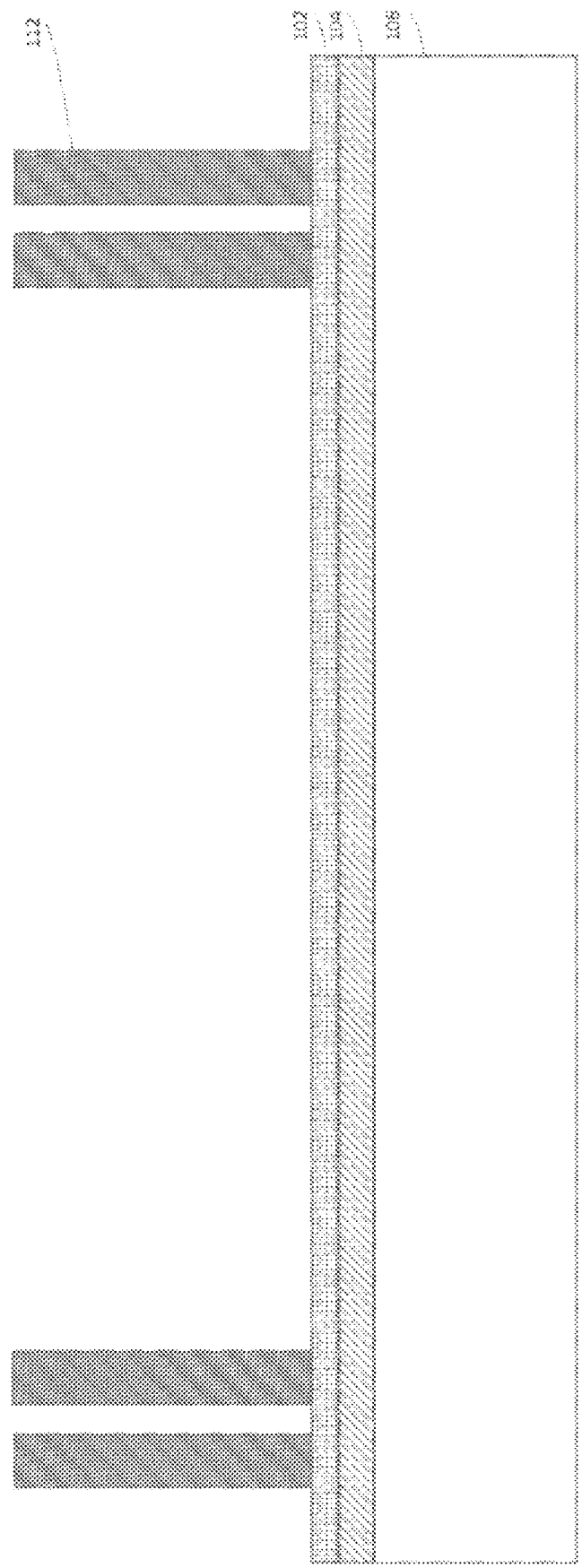

In FIG. 6, the resist layer 110 is removed. For example, a resist stripper may be used to remove the resist layer 110. Portions of the metal layer 108 that were previously under unexposed portions of the resist layer 110 are also removed. For example, an anisotropic etch may be used to remove the metal layer 108, in which the metal layer 108 is etched faster than the metal pillars 112.

Figure 7:
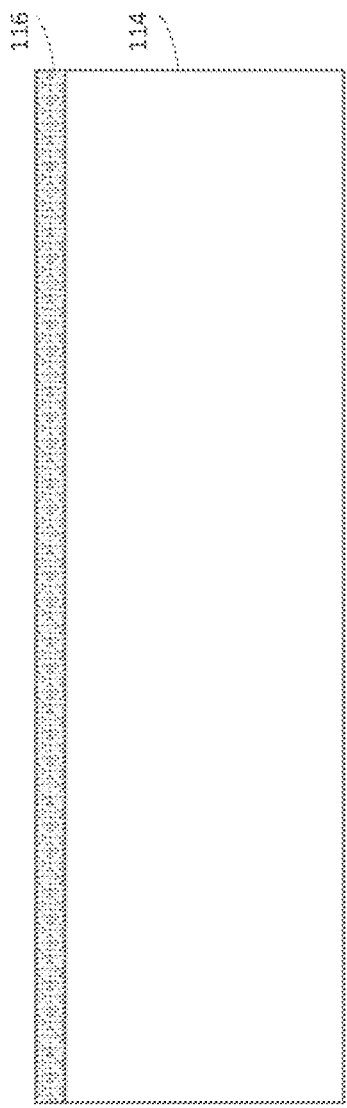

FIG. 7 illustrates an ultrasound-on-a-chip 114 coupled to an insulating layer 116.

Figure 8:
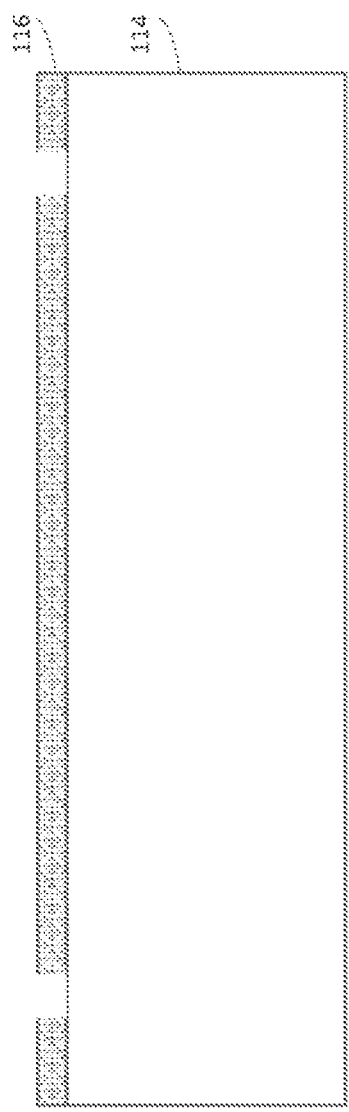

In FIG. 8, openings are created in the insulating layer 116 (e.g., using photolithography).

Figure 9:
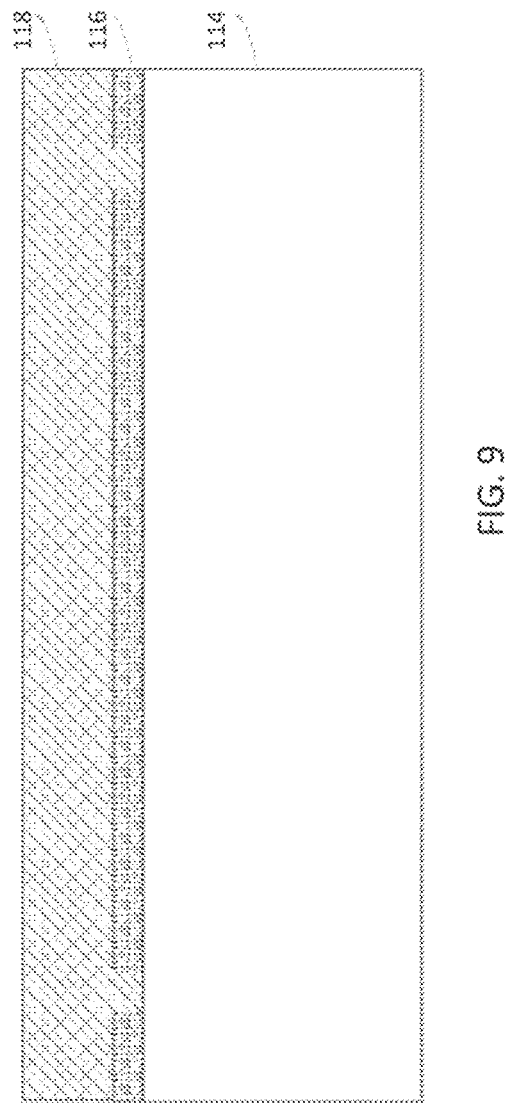

In FIG. 9, a resist layer 118 is formed on the insulating layer 116.

Figure 10:
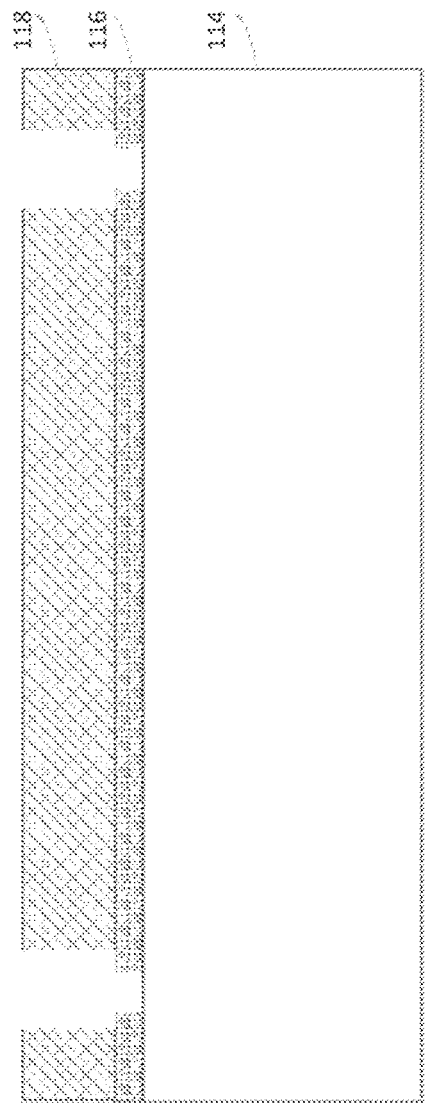

In FIG. 10, openings are created in the resist layer 118 (e.g., using photolithography), where the openings created in the resist layer 118 extend into the openings created in the insulating layer 116.

Figure 11:
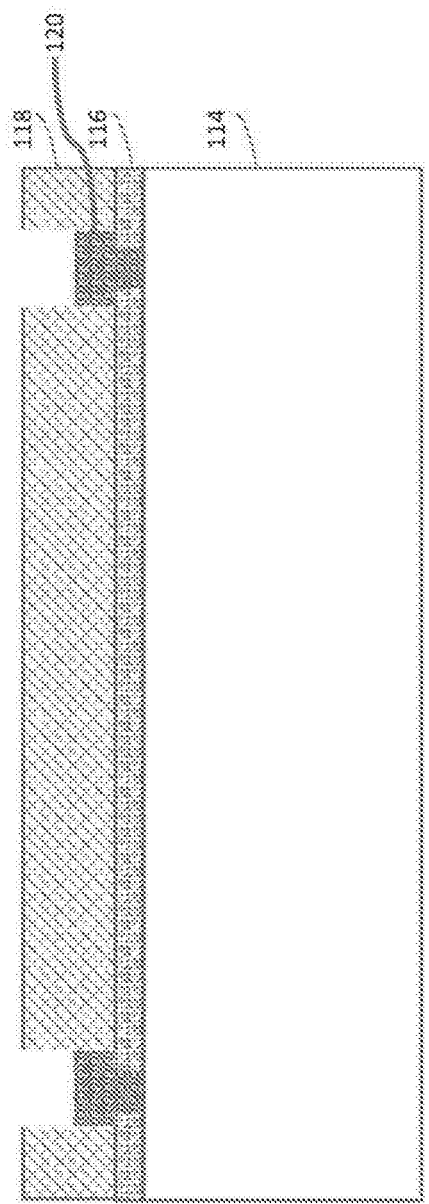

In FIG. 11, metal contacts 120 are formed within the openings in the resist layer 118 and the insulating layer 116. For example, the metal contacts 120 may be formed by electroplating, and may include copper or a copper alloy. In some embodiments, an under-bump metallurgy layer (not shown in FIG. 11) may be formed between the metal contacts 120 and the ultrasound-on-a-chip 114.

Figure 12:
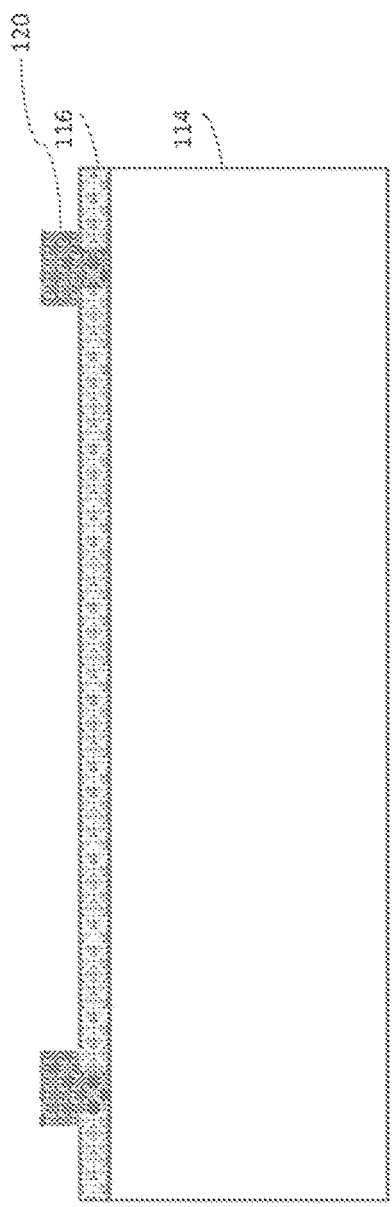

In FIG. 12, the resist layer 118 is removed (e.g., using a resist stripper).

Figure 13:
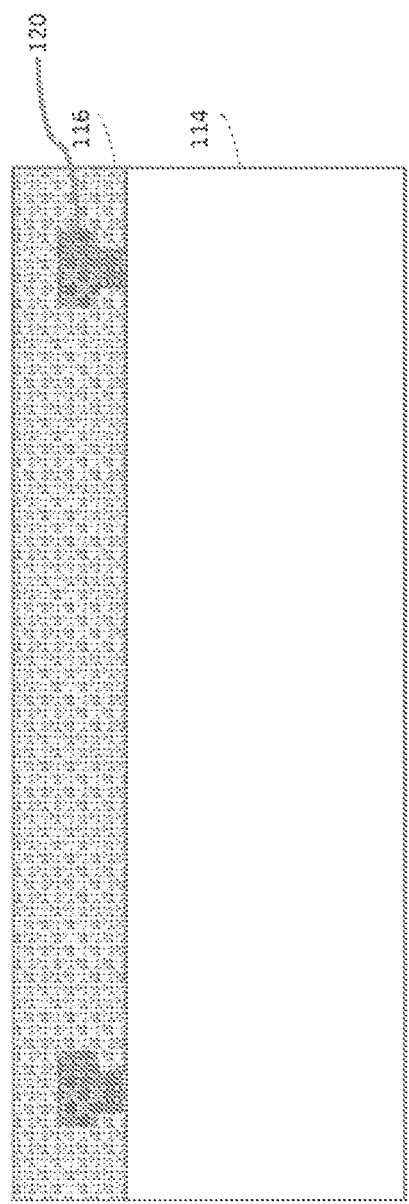

In FIG. 13, further insulating material is added to the insulating layer 116 to cover the metal contacts 120.

Figure 14:
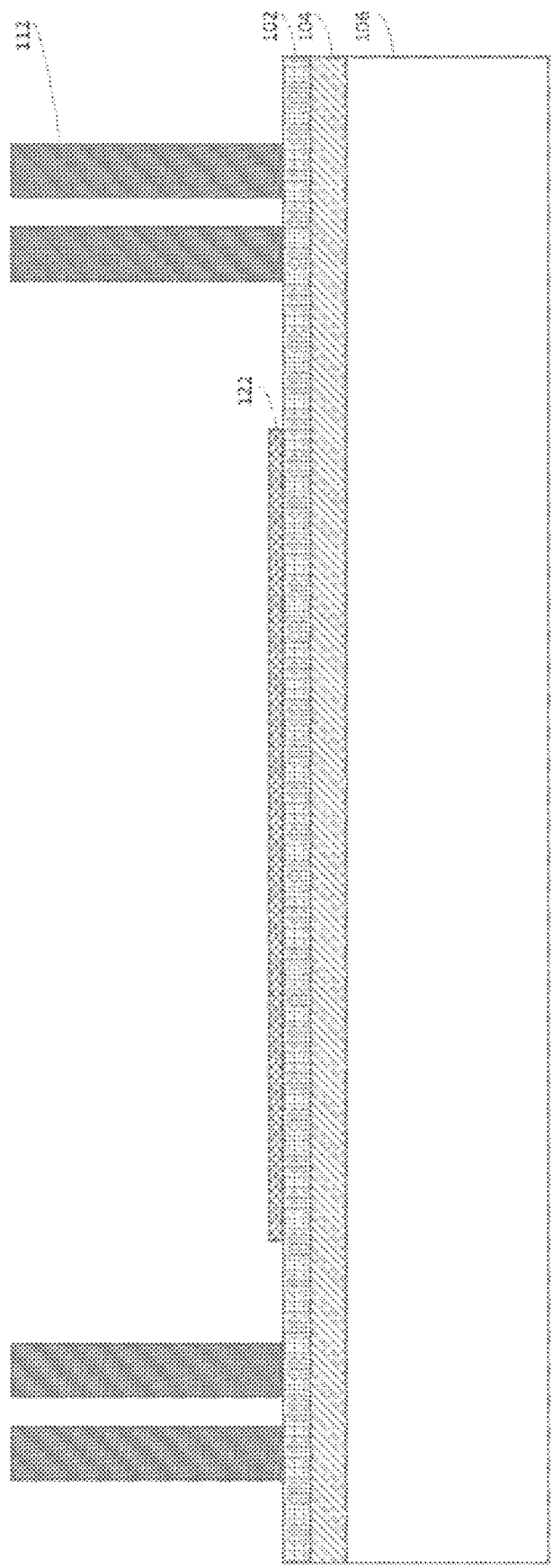

In FIG. 14, a die-attach film (DAF) 122 is coupled to the insulating layer 102.

Figure 15:
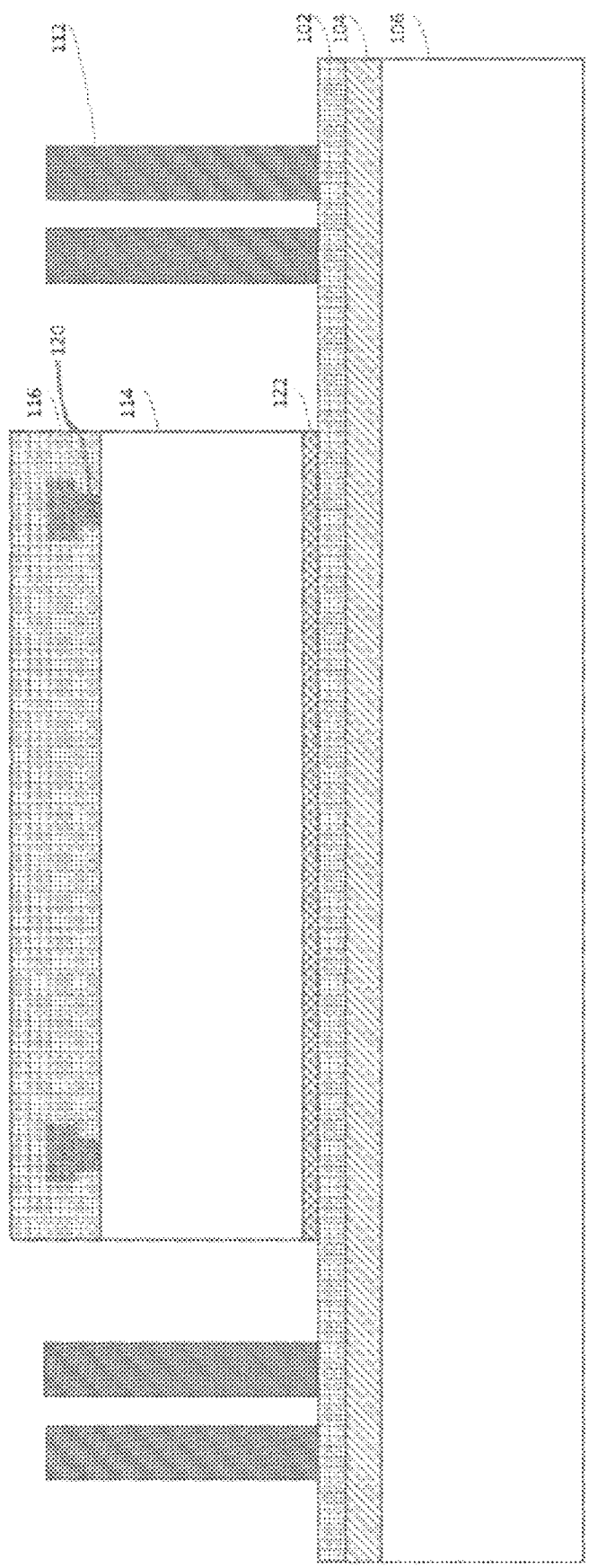

In FIG. 15, the ultrasound-on-a-chip 114 is coupled to the die-attached film 122.

Figure 16:
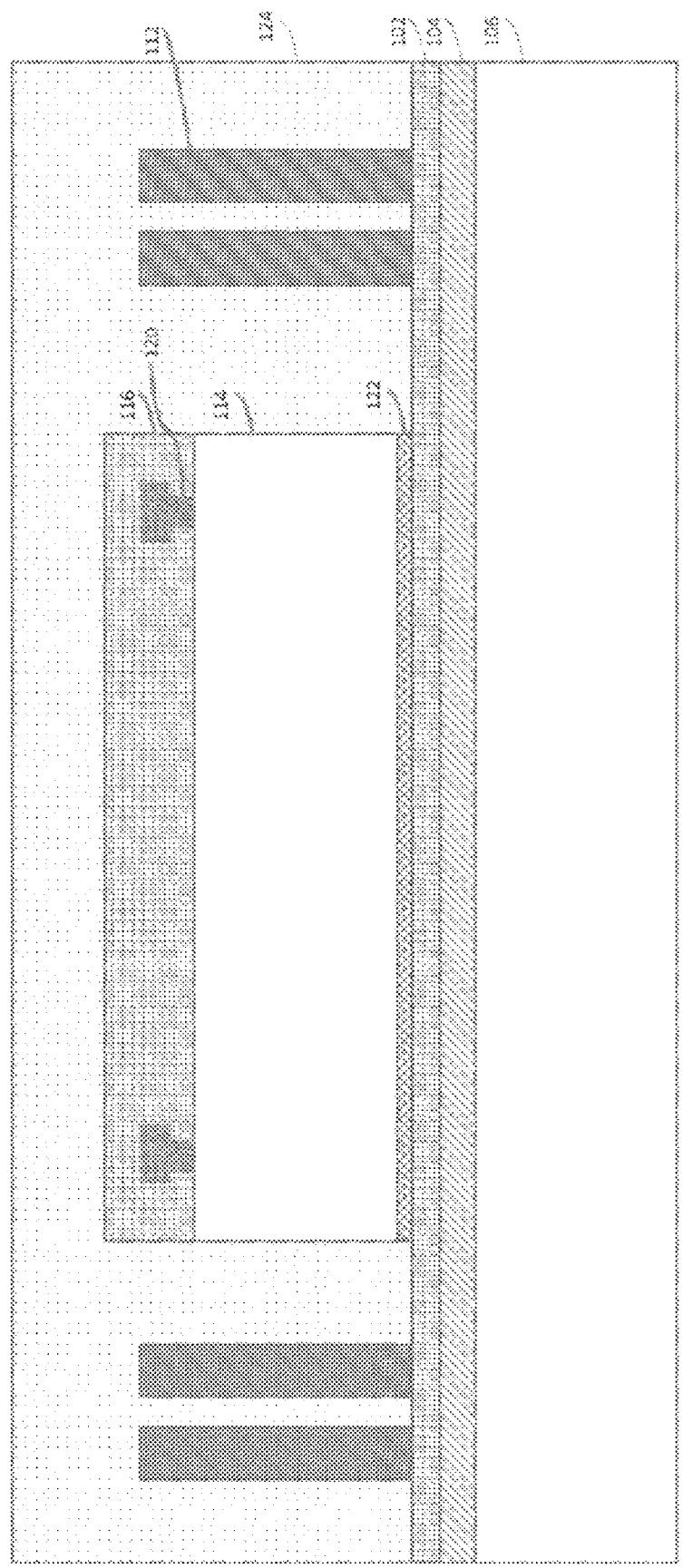

In FIG. 16, encapsulation 124 is formed to encapsulate the ultrasound-on-a-chip 114, the insulating layer 116, the die-attach film 122, and the metal pillars 112. The encapsulation 124 may include a molding compound, a molding underfill, an epoxy, or a resin. The top surface of the encapsulation 124 extends above the top surfaces of the insulating layer 116 and the metal pillars 112.

Figure 17:
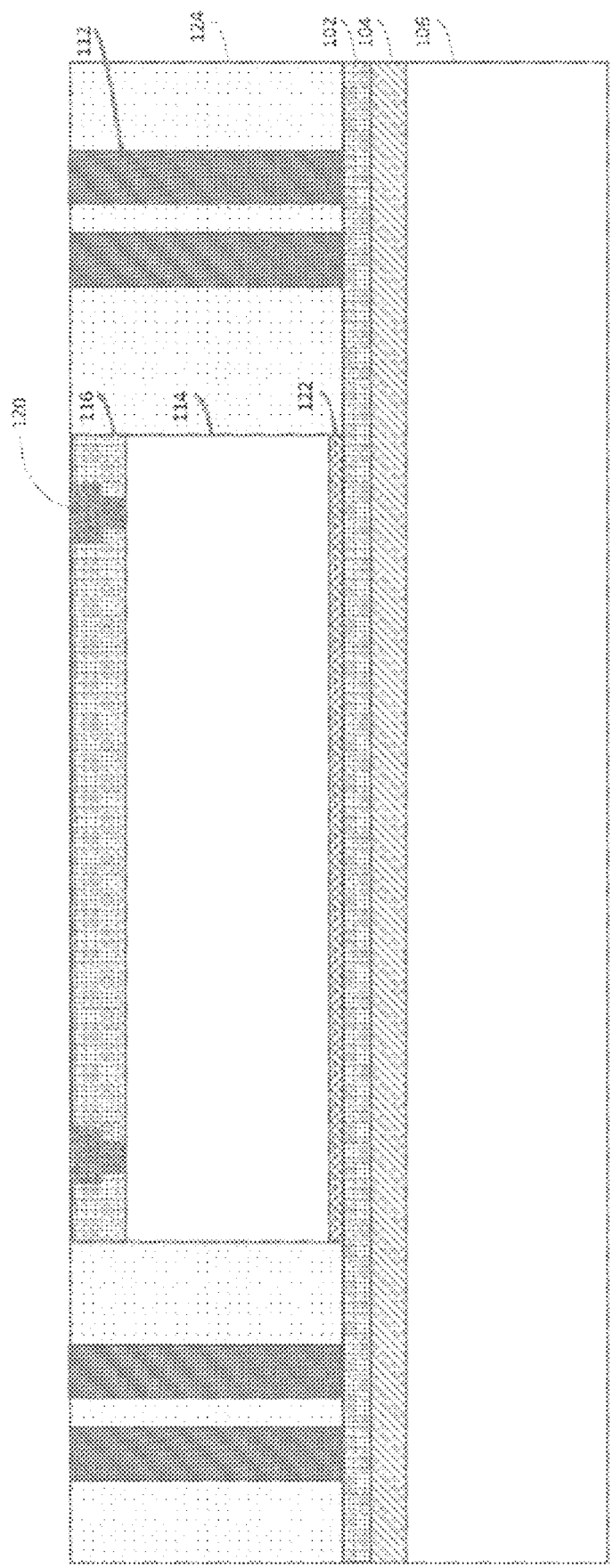

In FIG. 17, the top surfaces of the encapsulating 124 and the insulating layer 116 are planarized until the top surfaces of the top surfaces of the metal pillars 112 and the metal contacts 116 are exposed. For example, chemical mechanical planarization (CMP) may be used for the planarization.

Figure 18:
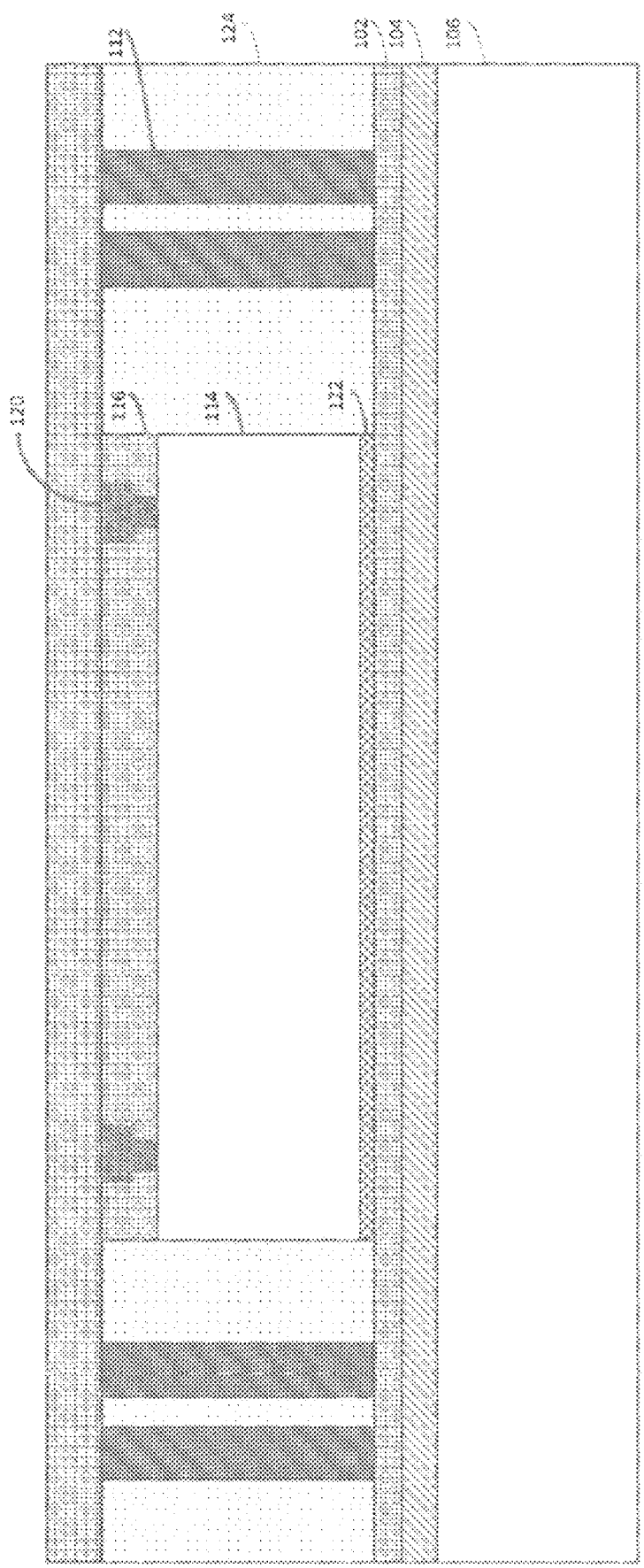

In FIG. 18, additional insulating material is added to the insulating layer 116, such that the insulating layer 116 covers the top surfaces of the metal contacts 120 and the metal pillars 112.

Figure 19:
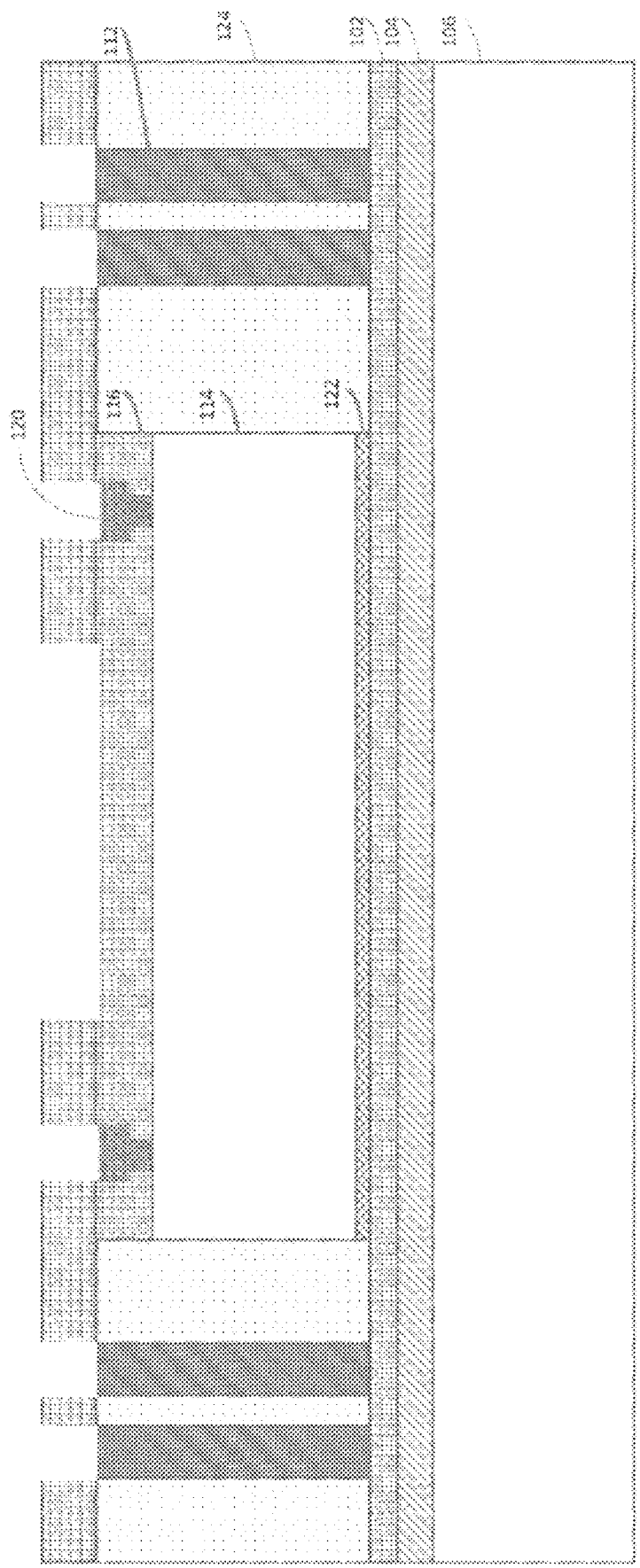

In FIG. 19, openings are created in the insulating layer 116 above the metal contacts 120 and the metal pillars 112. For example, photolithography may be used to create the openings.

Figure 20:
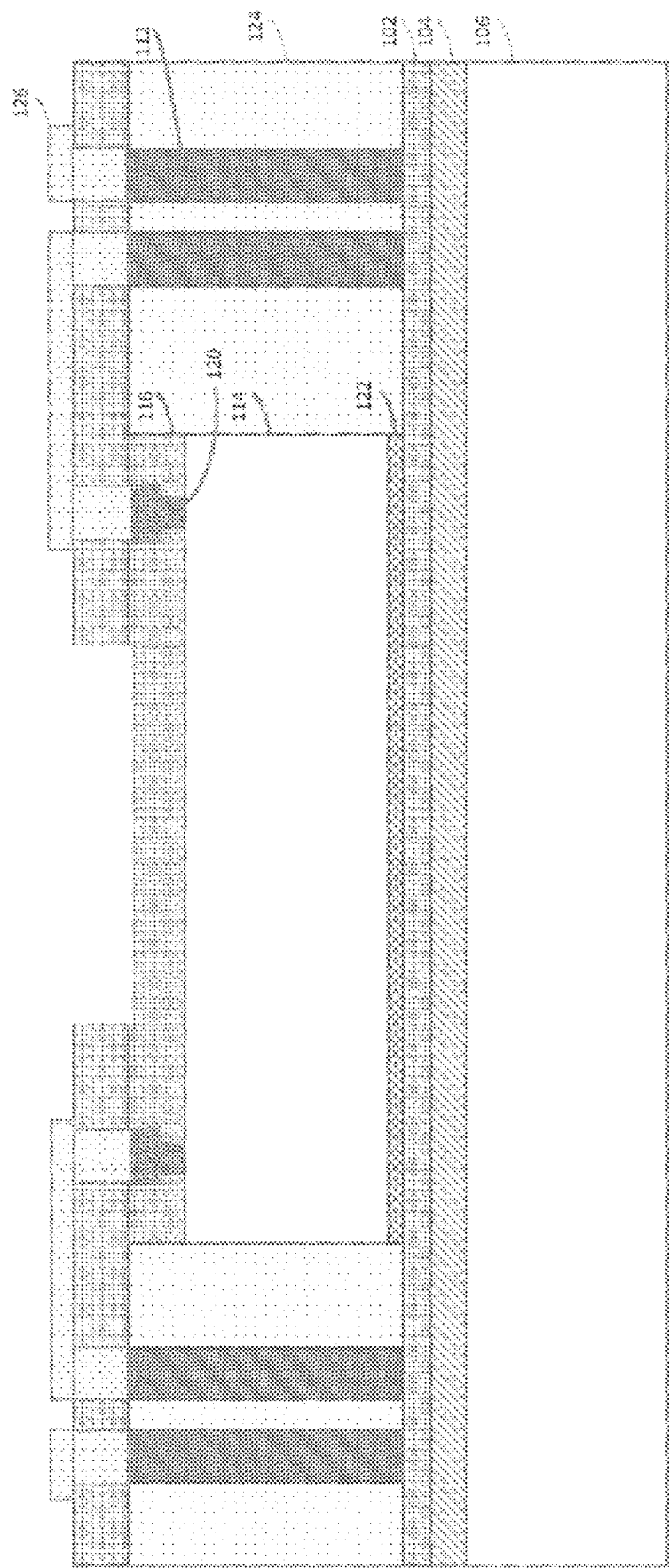

In FIG. 20, redistribution lines (RDL) 126 are formed in the openings in the insulating layer 116 and on the insulating layer 116. As shown, the RDL 126 may electrically connect certain of the metal contacts 120 to certain of the metal pillars 122. The RDL 126 may include metal traces and vias, may be formed using electroplating (including formation of a seed layer not shown), and may include metal such as aluminum, copper, tungsten, and/or alloys of these metals. The RDL 126 may include multiple layers of metal traces and vias.

Figure 21:
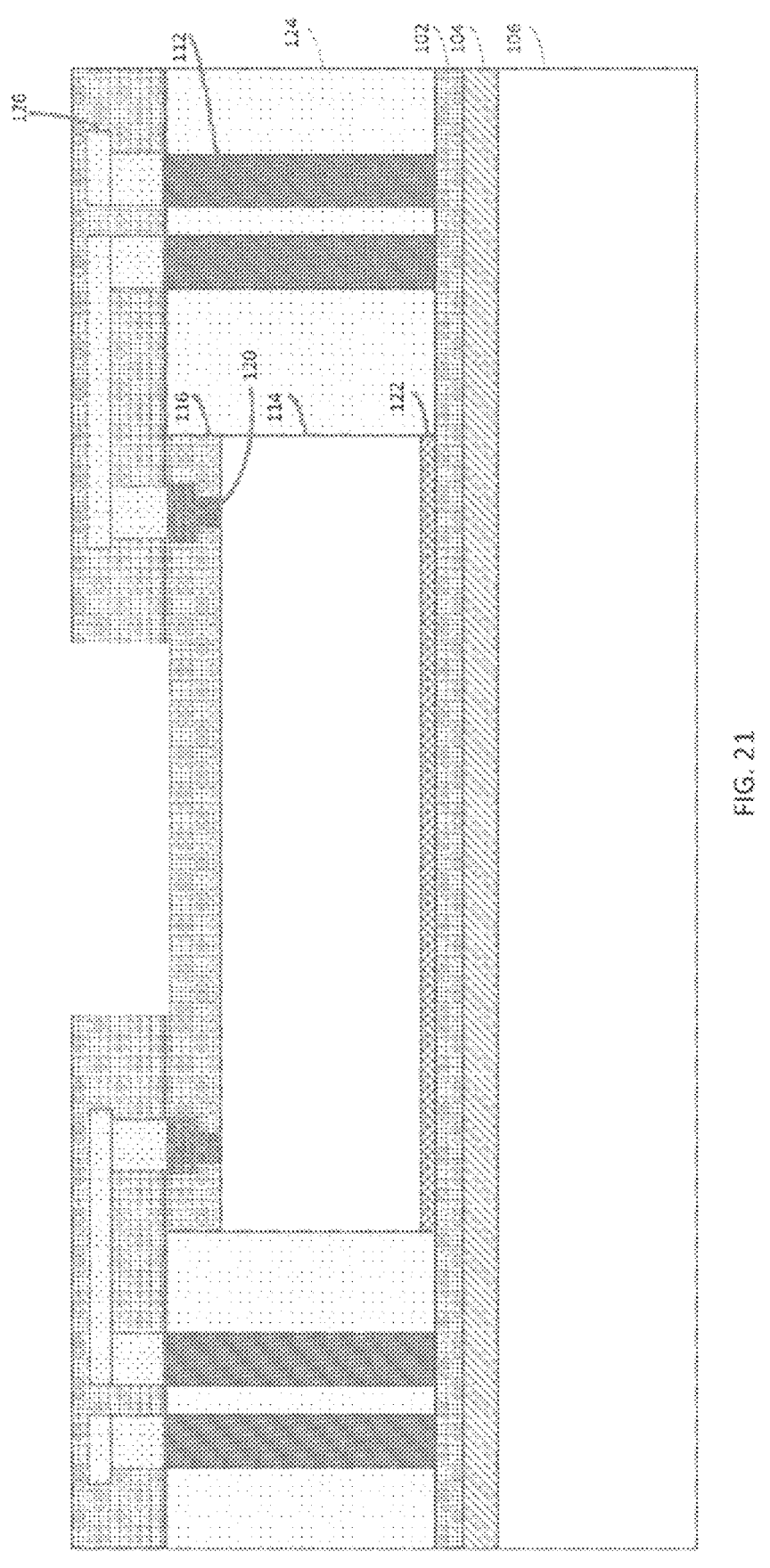

In FIG. 21, additional insulating material is added to the insulating layer 116 to cover the top surface of the RDL 126.

Figure 22:
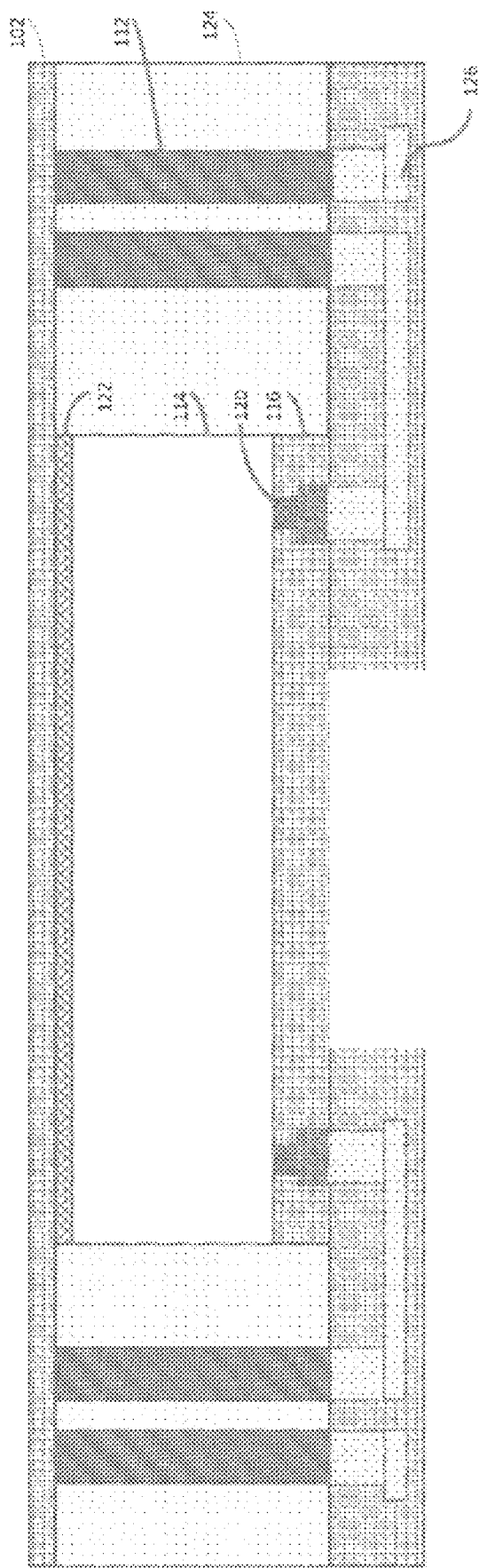

In FIG. 22, the carrier substrate 106 and the release layer 104 are detached from the insulating layer 102. For example, projecting light (e.g., ultraviolet or laser) onto the release layer 104 may decompose the release layer 104, causing the release layer 104 and the carrier substrate 106 to detach from the insulating layer 102. The surface of the insulating layer 102 may also be cleaned to remove any residue. The structure of FIG. 21 is flipped over to arrive at the orientation of FIG. 22.

Figure 23:
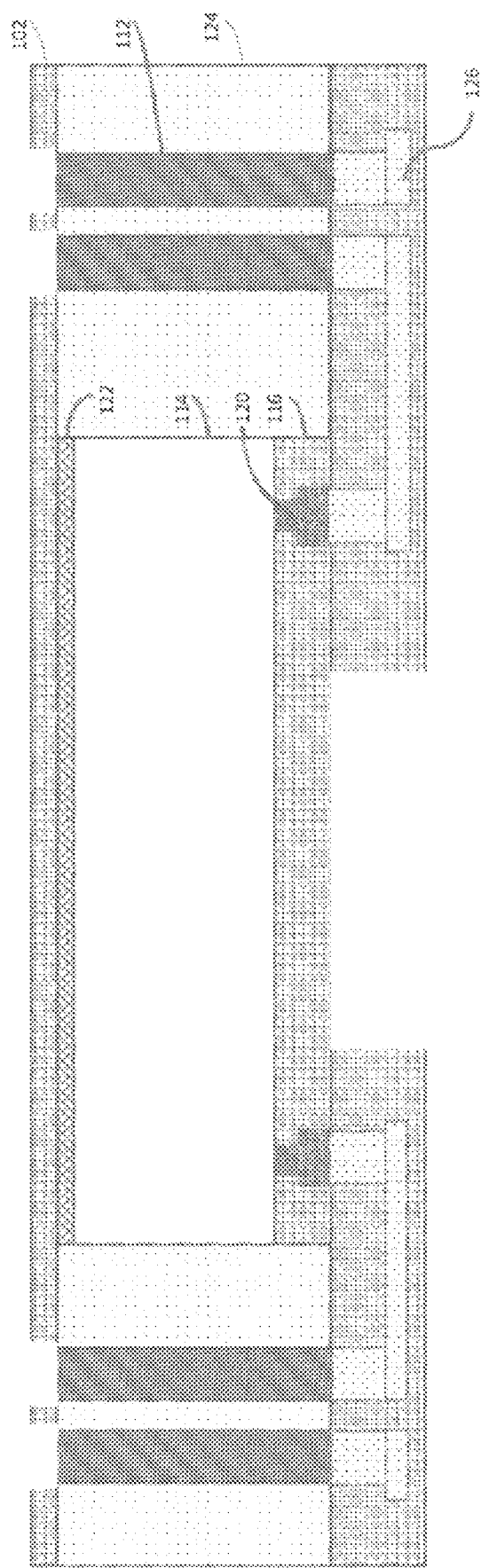

In FIG. 23, openings are created in the insulating layer 102.

Figure 24:
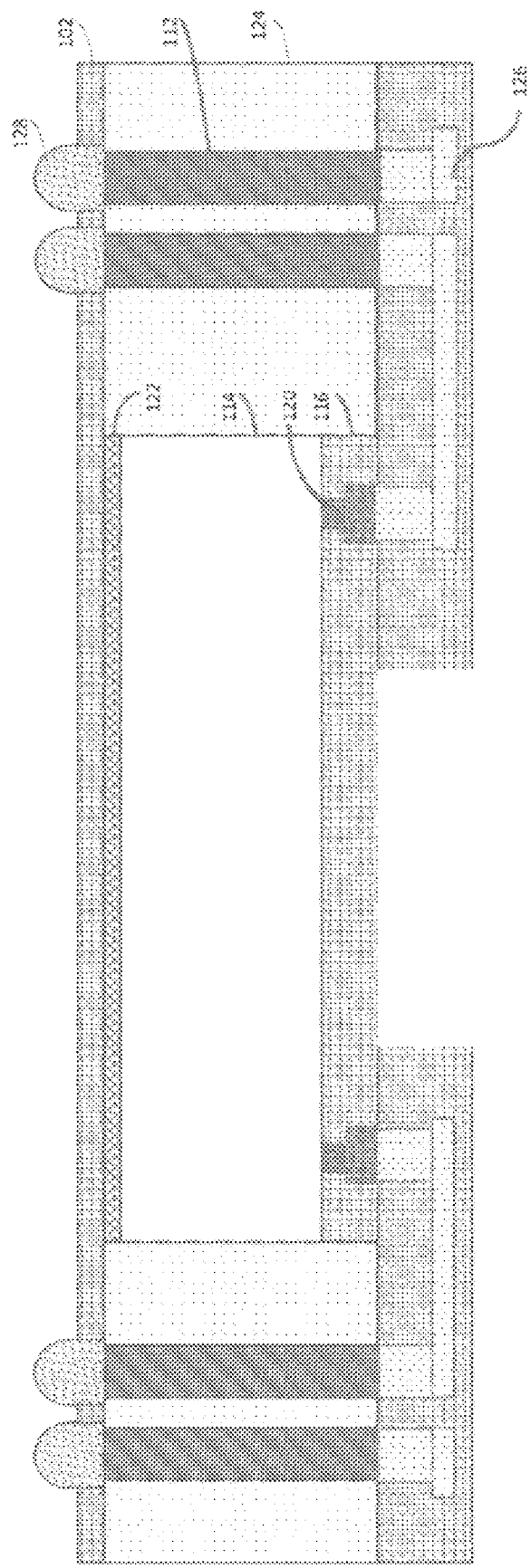

In FIG. 24, solder balls 128 are placed in the openings in the insulating layer 102. In some embodiments, the solder balls 128 may be formed by electroplating. In some embodiments, other forms of electrical connectors (e.g., metal pillars) may be formed in the openings. In some embodiments, an under-bump metallurgy layer (not shown in FIG. 24) may be formed between the solder balls 128 and the metal pillars 112.

Figure 25:
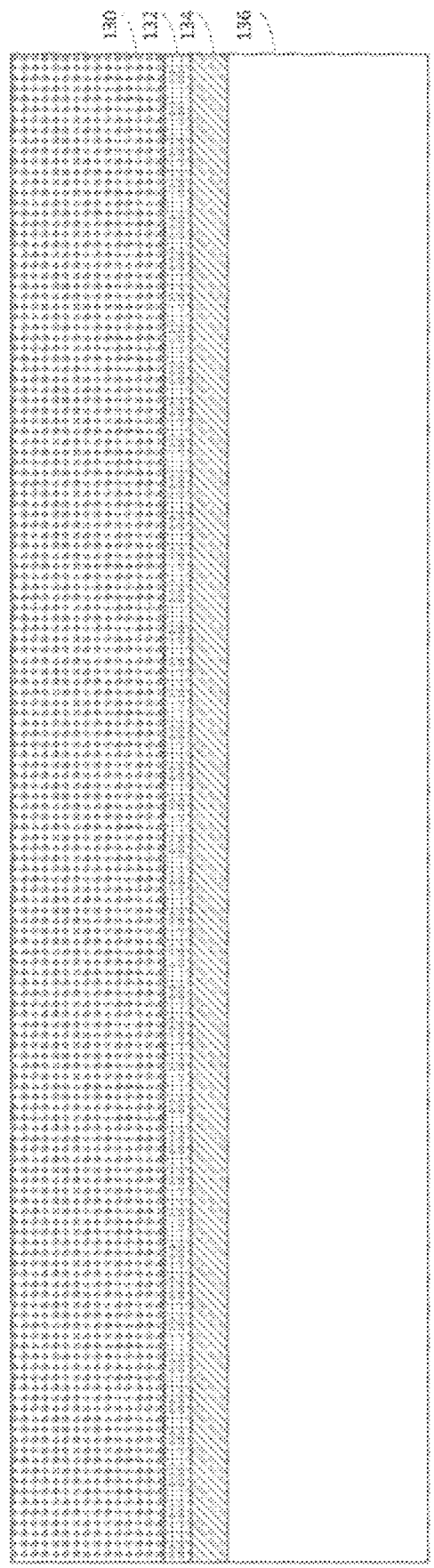

FIG. 25 illustrates a release layer 134 coupled to a carrier substrate 136, an insulating layer 132 coupled to the release layer 134, and an interposer layer 130 coupled to the insulating layer 132. The interposer layer 130 may include, for example, aluminum nitride.

Figure 26:
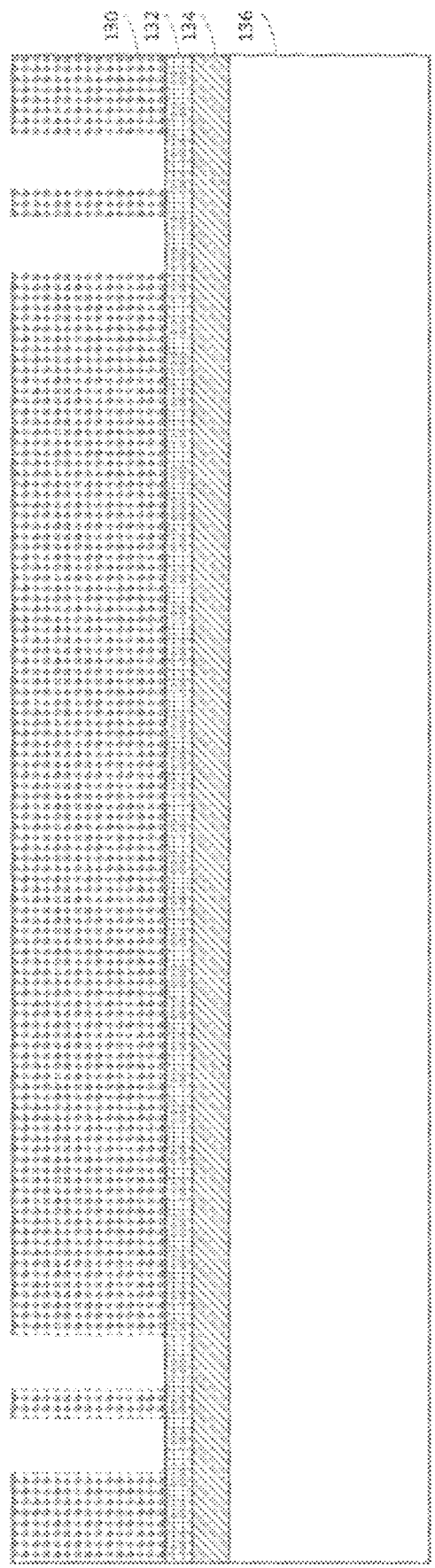

In FIG. 26, openings are formed in the interposer layer 130. For example, laser drilling may be used to form the openings.

Figure 27:
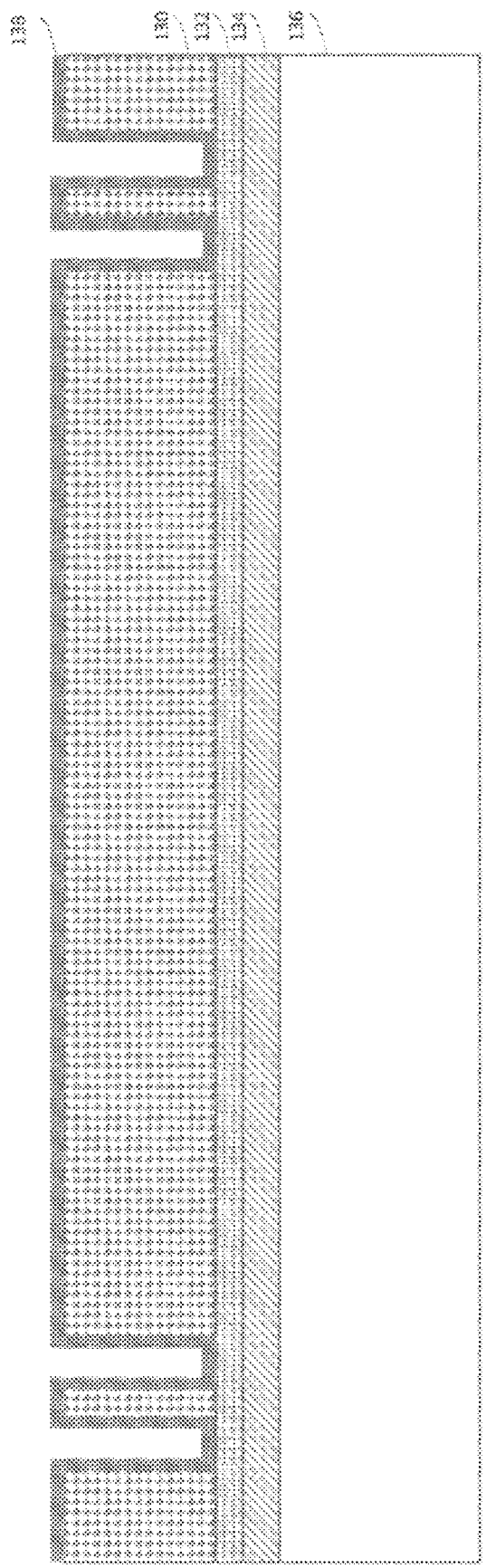

In FIG. 27, a metal layer 138 is formed on the interposer layer 130. The metal layer 138 may be formed, for example, using sputtering. The metal layer 138 may include, for example, copper, or in some embodiments, the metal layer 138 may include two layers, such as a titanium layer coupled to the interposer layer 130 and a copper layer coupled to the titanium layer.

Figure 28:
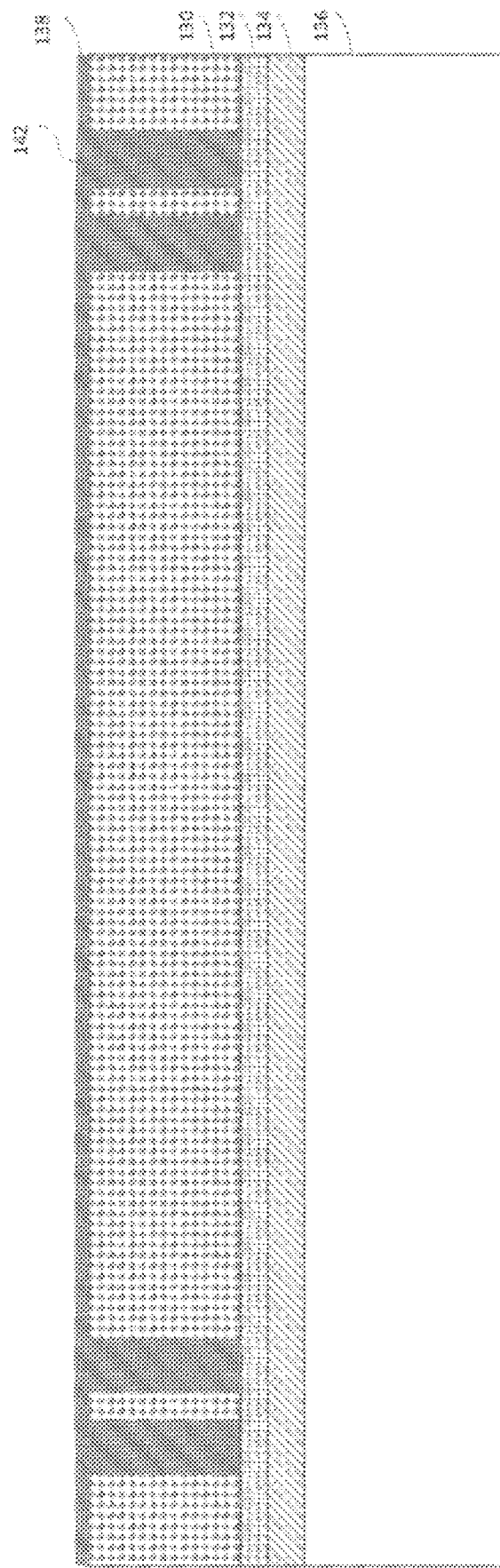

In FIG. 28, metal pillars 142 are formed in the openings in the resist layer 130 using electroplating. The metal layer 138 may serve as a seed layer for the electroplating. The metal pillars 142 may include the same material as the metal layer 138, such as copper. It should be appreciated that in addition to serving as electrical routing, the metal pillars 142 may also help to strengthen the interposer layer 130, which may be brittle.

Figure 29:
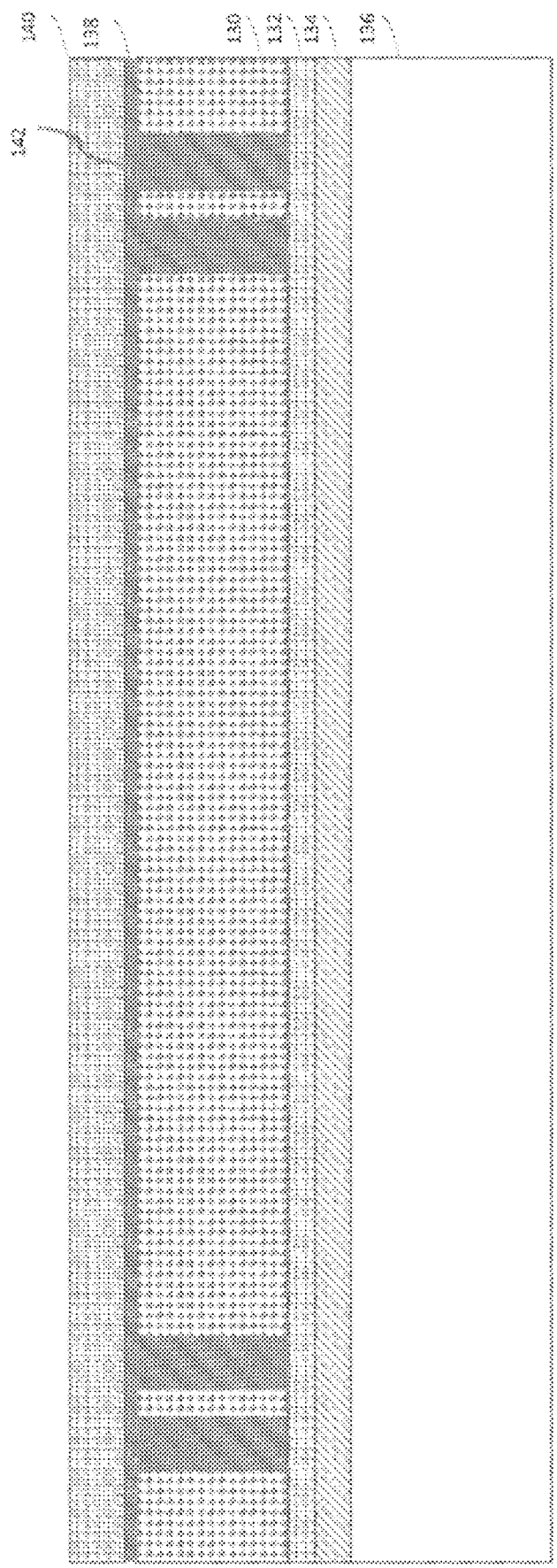

In FIG. 29, a resist layer 140 is formed on the metal layer 138 and the metal pillars 142.

Figure 30:
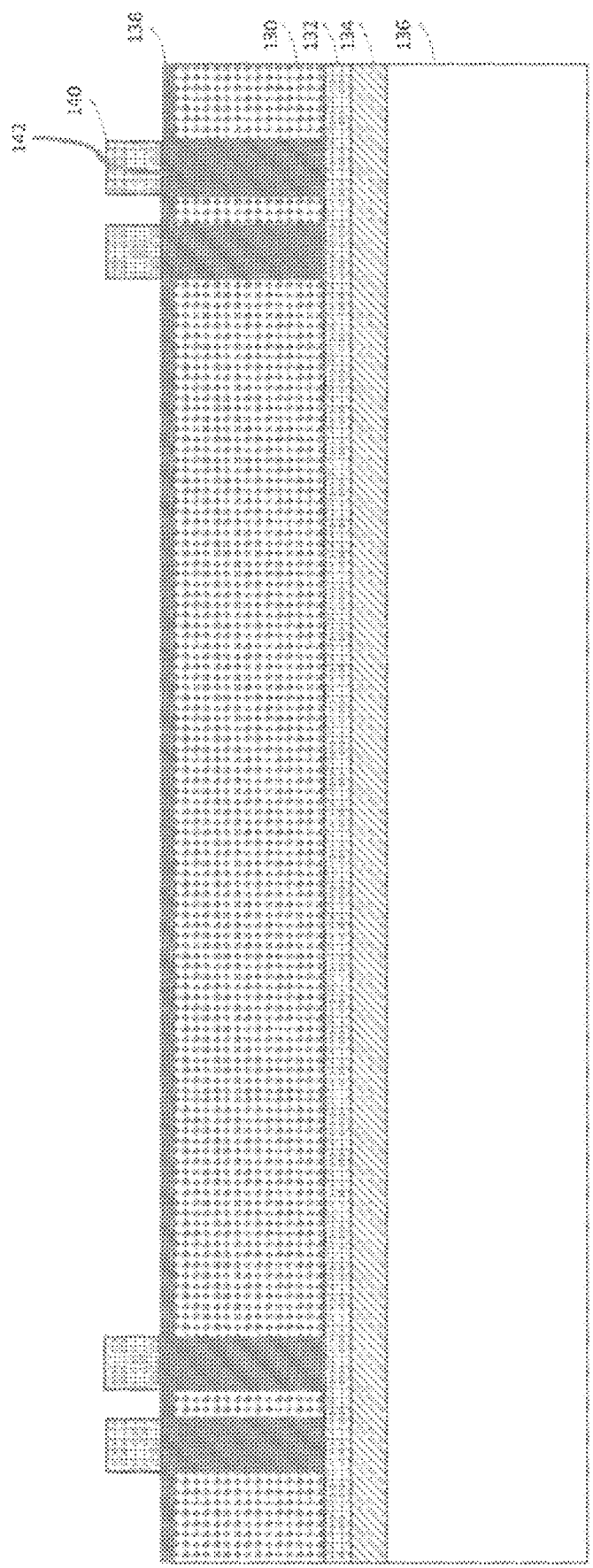

In FIG. 30, the resist layer 140 is patterned (e.g., using photolithography) to block the top surfaces of the metal pillars 142.

Figure 31:
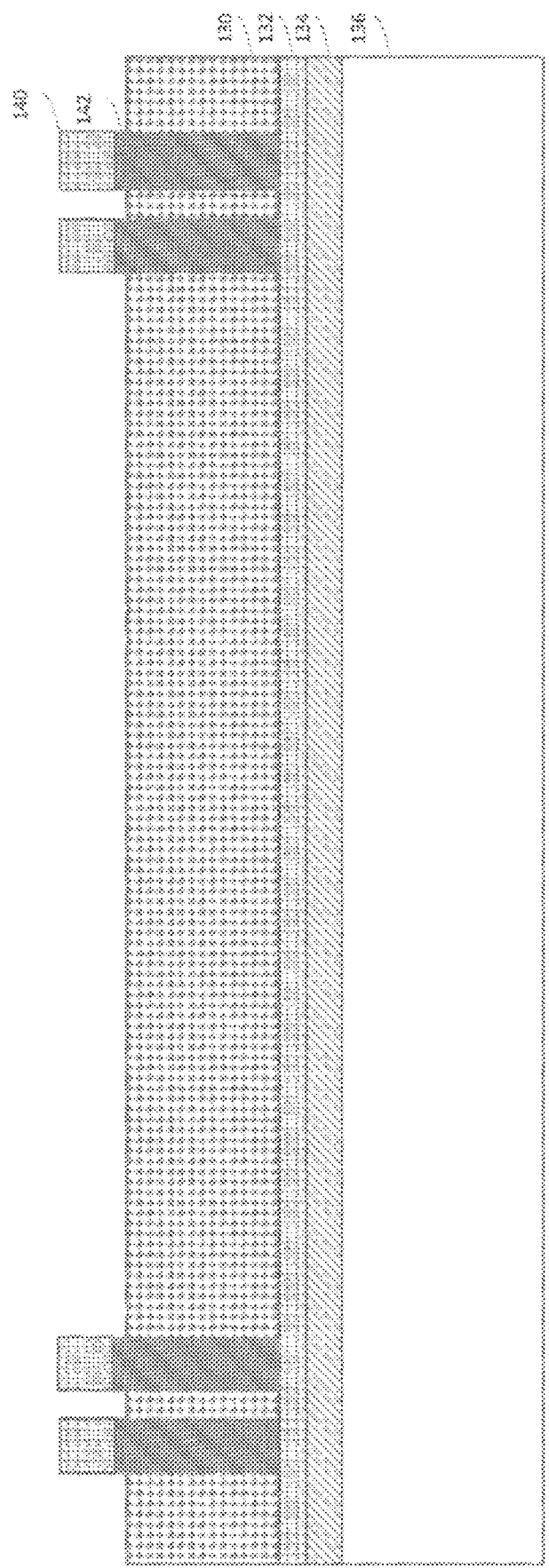

In FIG. 31, non-blocked portions of the metal layer 108 are etched to electrically isolate the metal pillars 142. In some embodiments, instead of or in addition to using photolithography to block the metal pillars 142, a timed etch or an anisotropic etch may be used.

Figure 32:
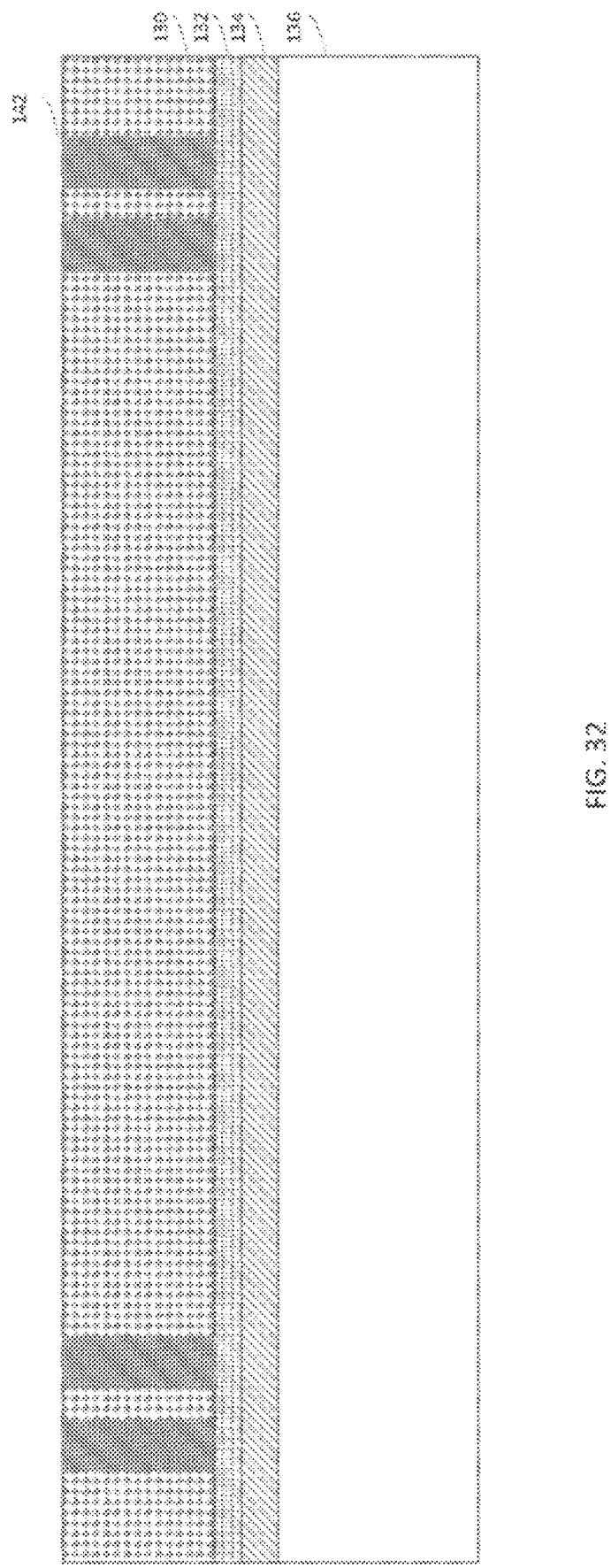

In FIG. 32, the resist layer 140 is removed (e.g., using resist stripper).

Figure 33:
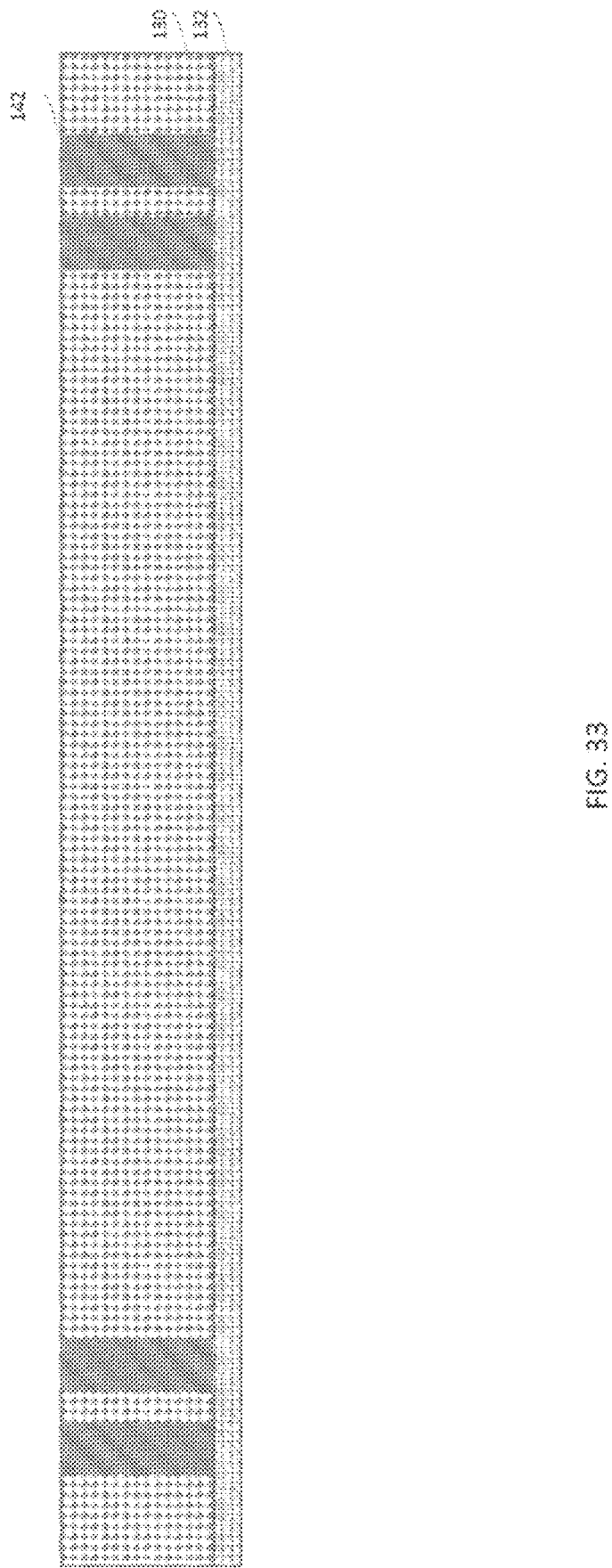

In FIG. 33, the carrier substrate 136 and the release layer 134 are detached from the insulating layer 132.

Figure 34:
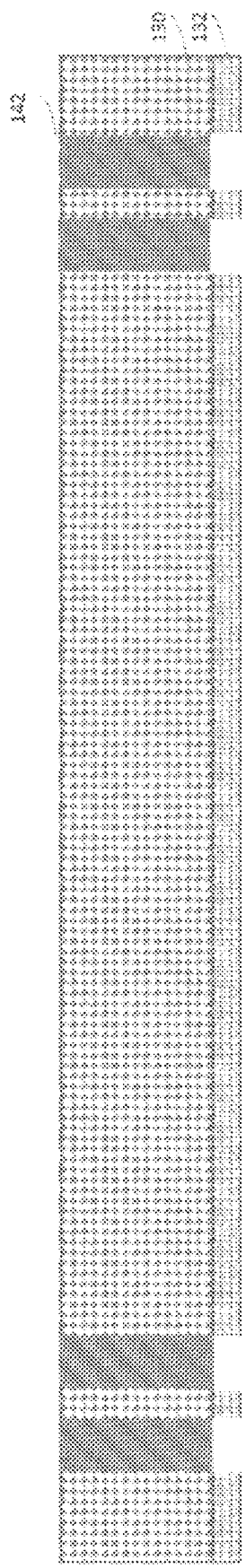

In FIG. 34, openings are created in the insulating later 132.

Figure 35:
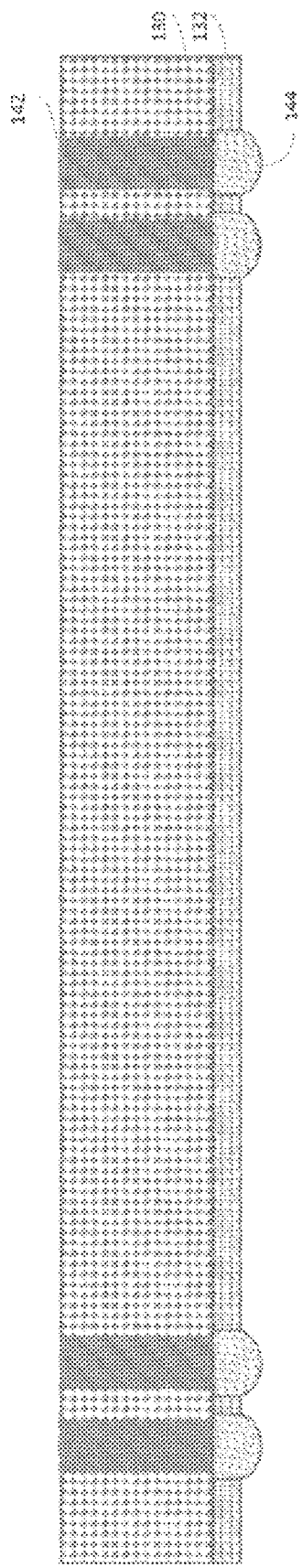

In FIG. 35, solder balls 144 are placed in the openings in the insulating layer 132.

Figure 36:
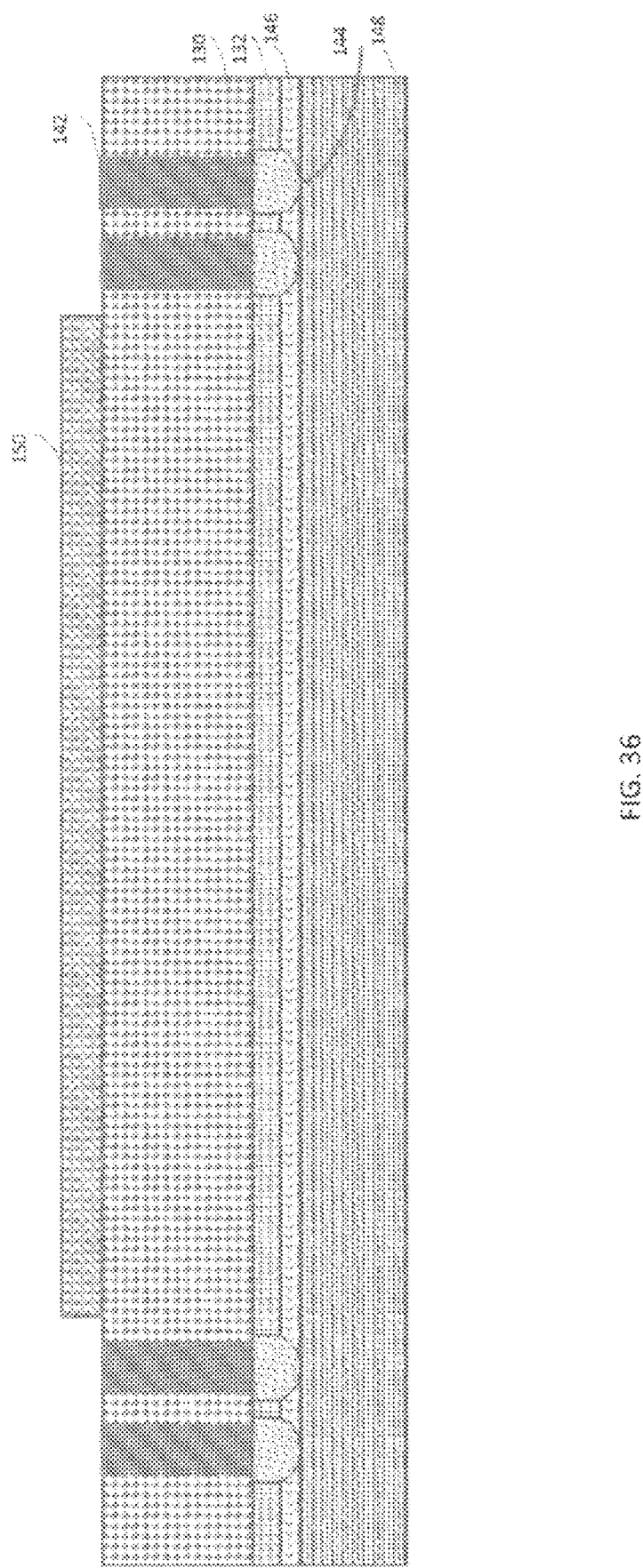

In FIG. 36, a thermal adhesive layer 150 is coupled to the interposer layer 142. In some embodiments, the thermal adhesive layer 150 may include a silver-containing epoxy. The solder balls 144 are coupled to a printer circuit board (PCB) 148. In some embodiments, surface-mount technology (SMT) or flip-chip soldering may be used to couple the solder balls 144 to the PCB 148. An underfill (e.g., epoxy) layer 146 is formed between the insulating layer 132 and the PCB 148.

Figure 37:
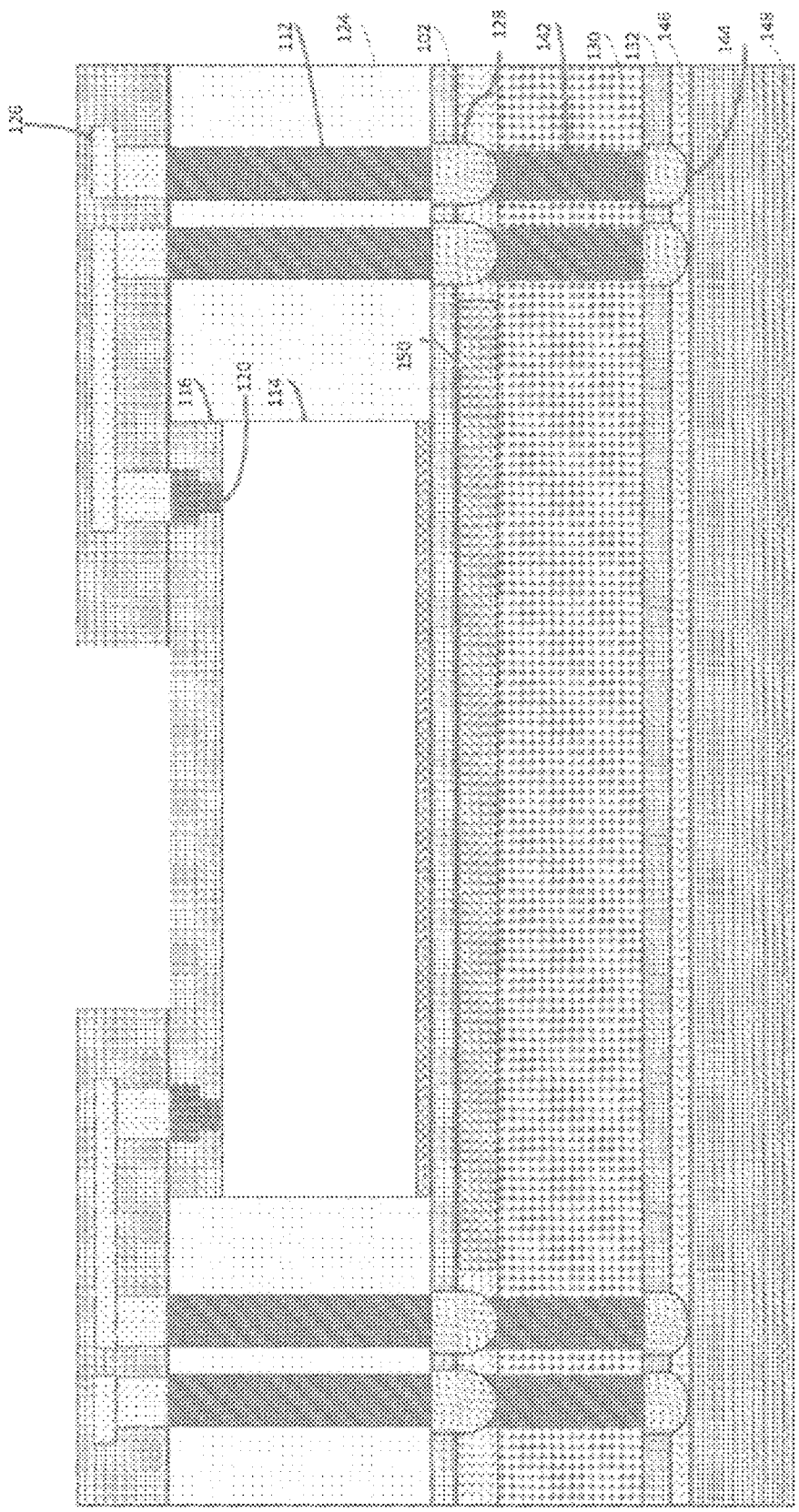

In FIG. 37, the solder balls 128 are coupled to the metal pillars 142. The metal pillars 112 are aligned with the metal pillars 142. In some embodiments, surface-mount technology (SMT) or flip-chip soldering may be used to couple the solder balls 128 to the metal pillars 142. In the final structure, the interposer may provide electrical routing between the ultrasound-on-a-chip 114 and the PCB 148, as well as a heatsink for the ultrasound-on-a-chip 114.

Figure 38:
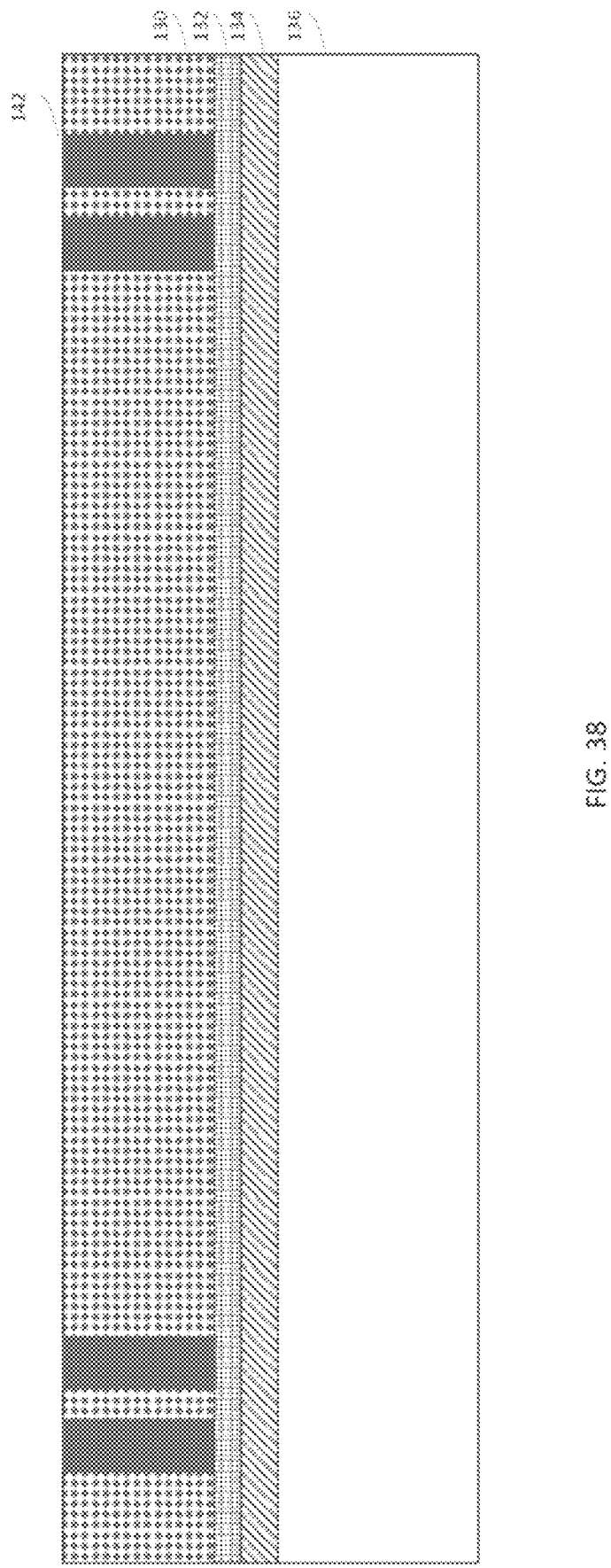
FIGS. 38-42 illustrate cross-sections of a various structures during packaging of an ultrasound-on-a-chip device using another process, in accordance with certain embodiments described herein.

FIGS. 38-42 illustrate cross-sections of various structures during packaging of an ultrasound-on-a-chip device using another process, in accordance with certain embodiments described herein. FIG. 38 illustrates the structure of FIG. 32.

Figure 39:
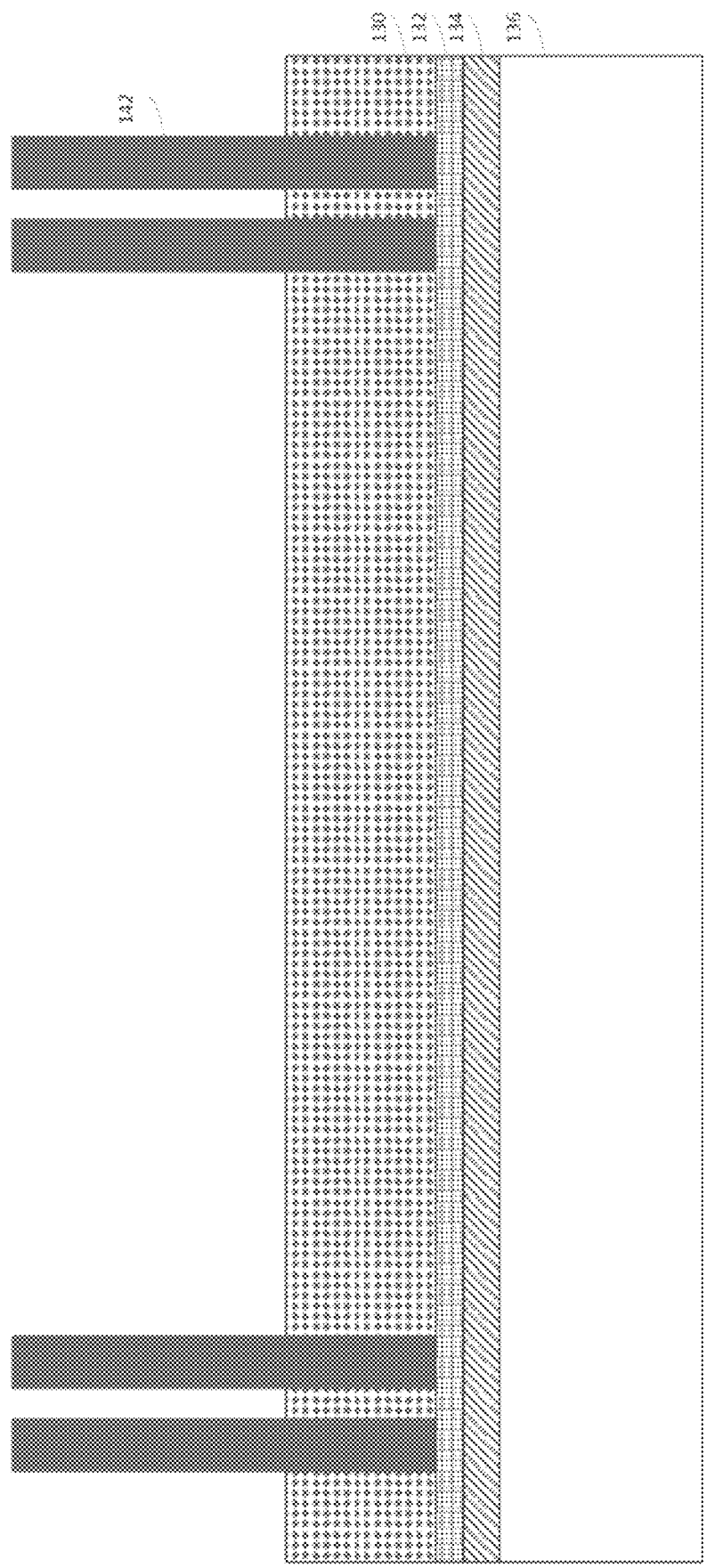

In FIG. 39, the metal pillars 142 are extended upwards using electroplating. As can be seen, the metal pillars 142 extend beyond the top surface of the interposer layer 130.

Figure 40:
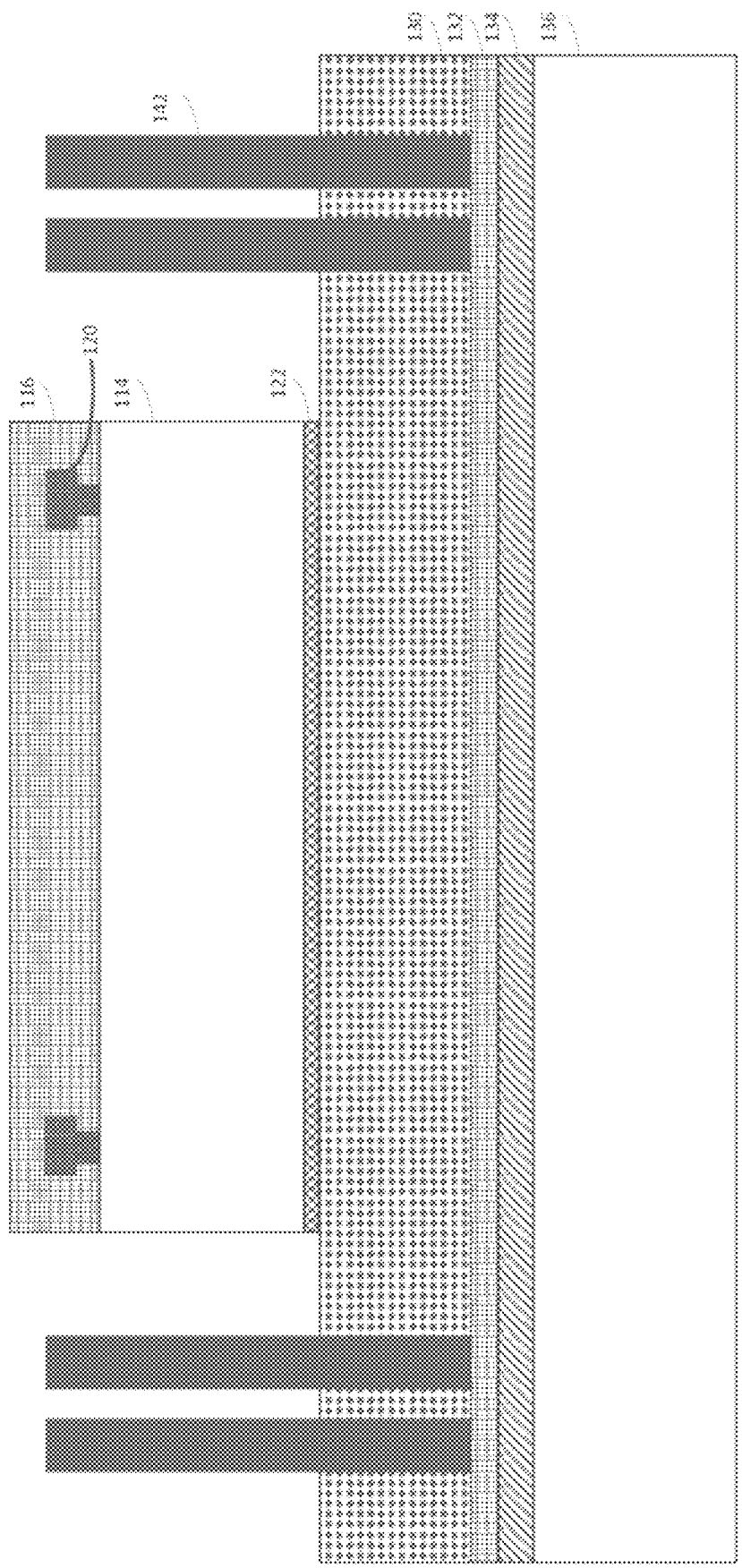

In FIG. 40, the ultrasound-on-a-chip 114 is coupled to the interposer layer 130 through the die-attach film 122.

Figure 41:
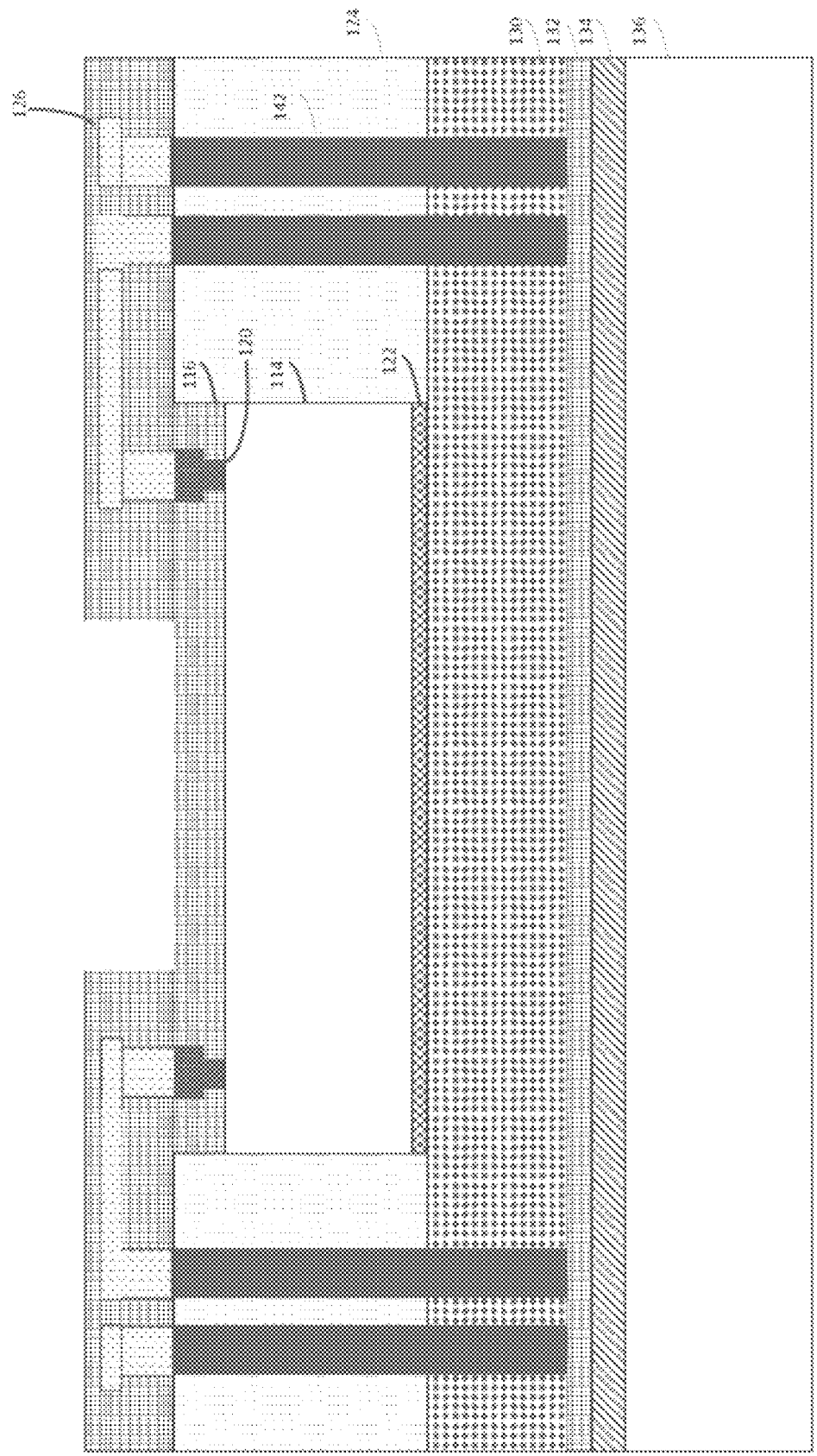

In FIG. 41, further insulating material is added to the insulating layer 116. The encapsulation 124 is formed to encapsulate the ultrasound-on-a-chip 114, the insulating layer 116, the die-attach film 122, and the metal pillars 142, similar to in FIG. 16. The RDL 126 is formed, similar to in FIGS. 18-21.

Figure 42:
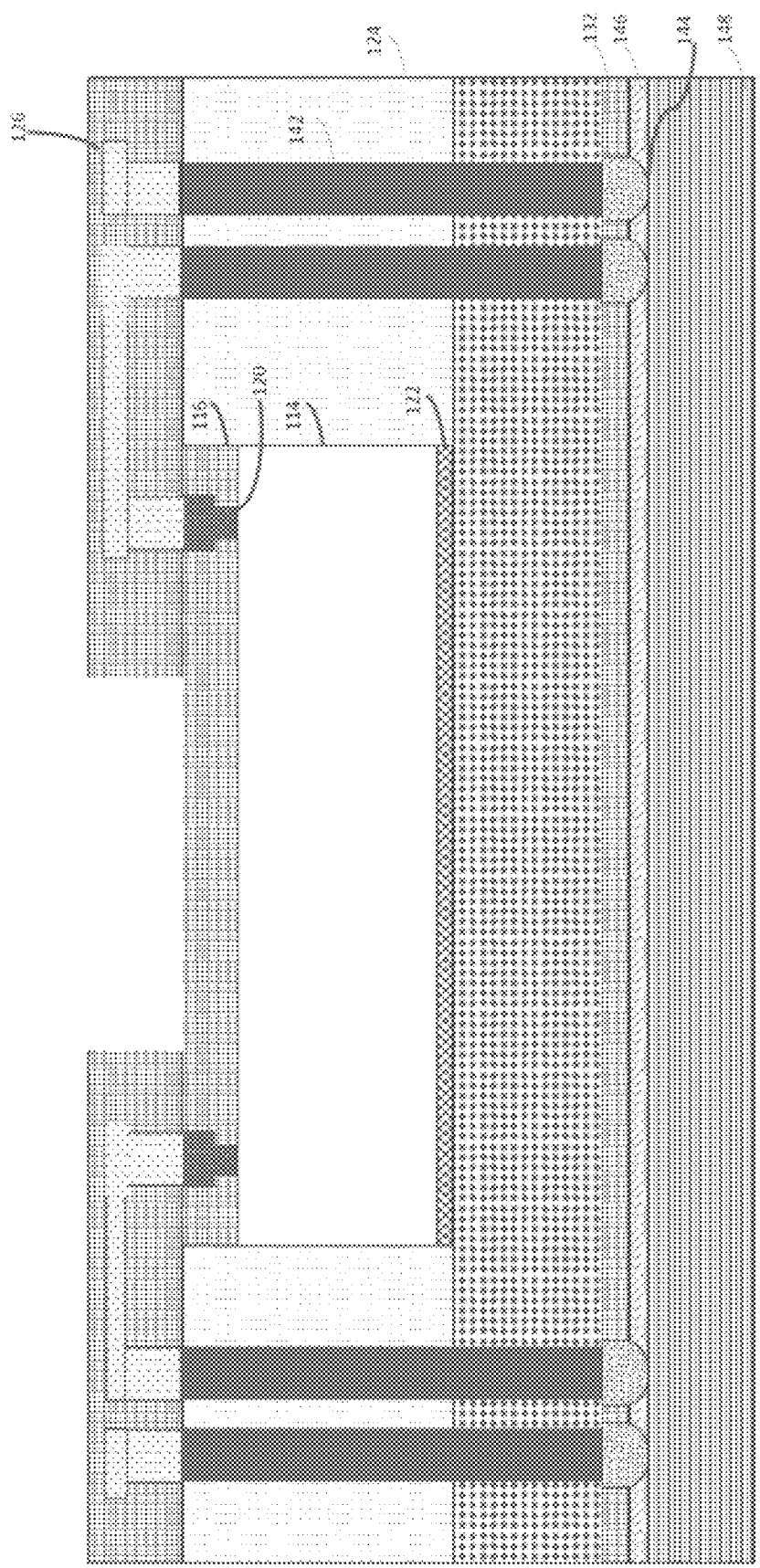

In FIG. 42, the carrier substrate 136 and the release layer 134 are detached from the insulating layer 132, the solder balls 144 are formed on the metal pillars 142, the solder balls 144 are coupled to the PCB 148, and an underfill layer 146 is formed between the insulating layer 132 and the PCB 148, similar to in FIGS. 33-36.

Compared with the process of FIGS. 1-37, the process of FIGS. 38-42 may enable the ultrasound-on-a-chip 114 to be bound to the interposer layer 130 in a semiconductor foundry, where process control, quality, and yield may be high. Additionally, while the process of FIGS. 1-37 may require simultaneous bonding of the solder balls 128 to the metal pillars 142 and bonding of the insulating layer 102 to the thermal adhesive 150, the process of FIGS. 38-42 may eliminate the thermal adhesive layer 150.

Figure 43:
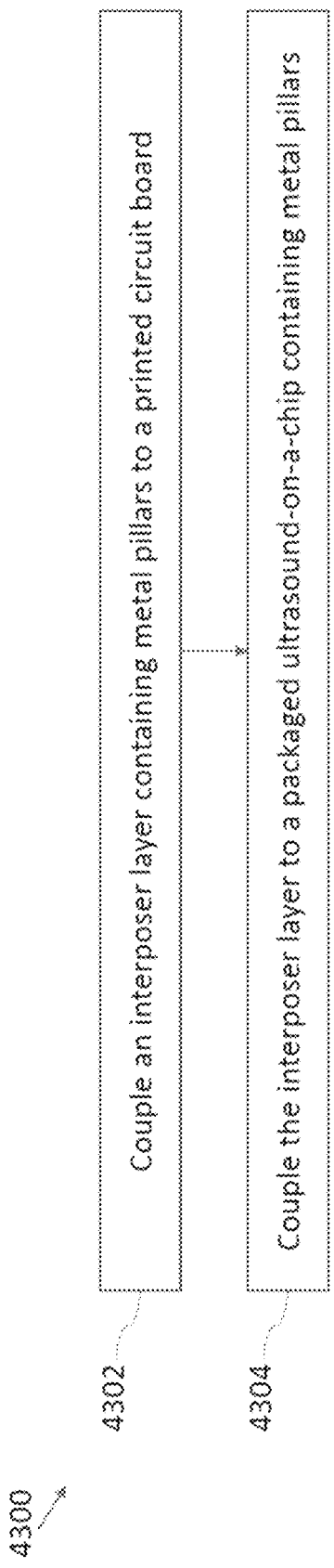
FIG. 43 illustrates an example process for packaging an ultrasound-on-a-chip, in accordance with certain embodiments described herein.

FIG. 43 illustrates an example process 4300 for packaging an ultrasound-on-a-chip, in accordance with certain embodiments described herein. In act 4302, an interposer layer containing metal pillars is coupled to a printed circuit board. Act 4302 may correspond to the step illustrated in FIG. 36. In act 4304, the interposer layer is coupled to a packaged ultrasound-on-a-chip containing metal pillars. Act 4304 may correspond to the step illustrated in FIG. 37. The interposer layer may be coupled to the packaged ultrasound-on-a-chip through a thermal adhesive layer.

Figure 44:
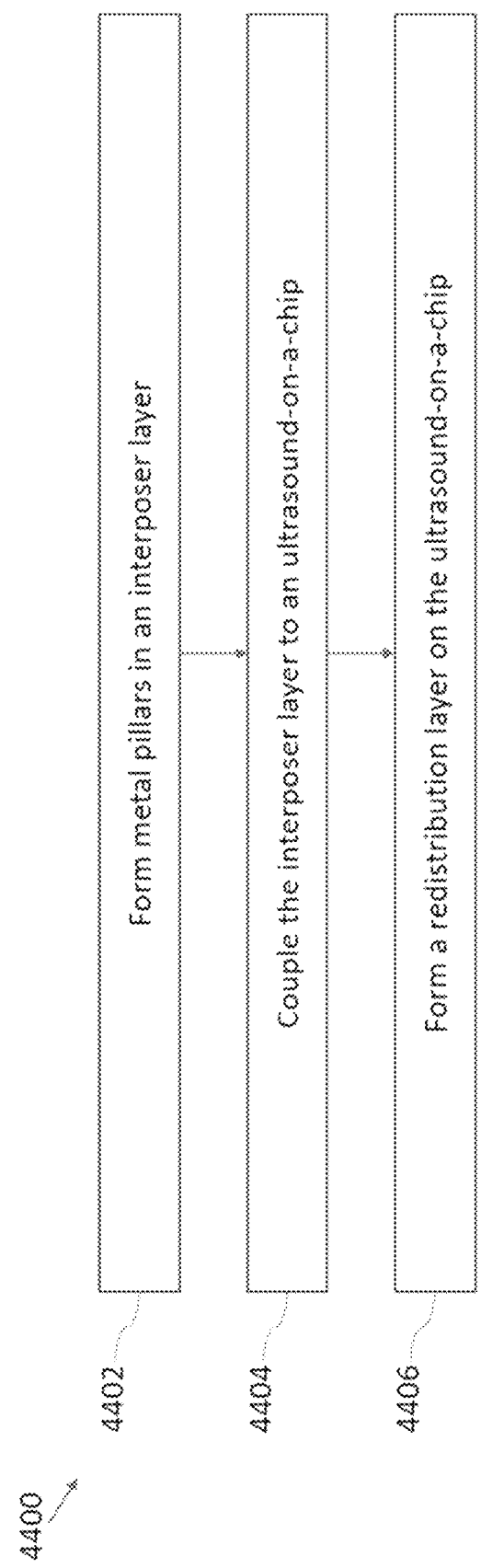
FIG. 44 illustrates an example process for packaging an ultrasound-on-a-chip, in accordance with certain embodiments described herein.

FIG. 44 illustrates an example process 4400 for packaging an ultrasound-on-a-chip, in accordance with certain embodiments described herein. In act 4402, metal pillars are formed in an interposer layer. Act 4402 may correspond to the steps illustrated in FIGS. 38-39. In act 4404, the interposer layer is coupled to an ultrasound-on-a-chip. Act 4404 may correspond to the step illustrated in FIG. 40. In act 4406, a redistribution layer is formed on the packaged ultrasound-on-a-chip. Act 4406 may correspond to the step illustrated in FIG. 41.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
   an ultrasound-on-a-chip device comprising a top surface and a bottom surface;
   a redistribution layer, wherein the top surface of the ultrasound-on-a-chip device is coupled to the redistribution layer;
   encapsulation encapsulating the ultrasound-on-a-chip device;
   first metal pillars extending through the encapsulation and electrically coupling to the redistribution layer; and
   an interposer layer comprising a top surface and a bottom surface, wherein the bottom surface of the ultrasound-on-a chip device is coupled to the top surface of the interposer layer.

2. The apparatus of claim 1, wherein the interposer layer comprises second metal pillars extending through the interposer layer.

3. The apparatus of claim 2, wherein the interposer layer comprises aluminum nitride.

4. The apparatus of claim 2, wherein the first metal pillars are electrically coupled to the second metal pillars.

5. The apparatus of claim 2, wherein the first metal pillars are aligned with the second metal pillars.

6. The apparatus of claim 2, wherein solder balls electrically couple the first metal pillars to the second metal pillars.

7. The apparatus of claim 2, further comprising a printed circuit board coupled to the bottom surface of the interposer layer.

8. The apparatus of claim 7, wherein solder balls electrically couple the second metal pillars to the printed circuit board.

9. The apparatus of claim 1, further comprising a printed circuit board coupled to the bottom surface of the interposer layer.

10. The apparatus of claim 1, wherein the ultrasound-on-a-chip is coupled to the interposer layer through thermal adhesive.

11. The apparatus of claim 10, further comprising a printed circuit board coupled to the bottom surface of the interposer layer.

12. The apparatus of claim 11, wherein solder balls electrically couple the first metal pillars to the printed circuit board.

13. The apparatus of claim 1, further comprising
   second metal pillars extending through the interposer layer and the encapsulation and electrically coupled to the redistribution layer.

14. The apparatus of claim 13, wherein the interposer layer comprises aluminum nitride.

15. The apparatus of claim 1, wherein the encapsulation is one of a molding compound, a molding underfill, an epoxy, or a resin.

16. The apparatus of claim 1, wherein the encapsulation fills spaces between the ultrasound-on-a-chip device and the first metal pillars.

* * * * *